(12) United States Patent
Kirschman

(10) Patent No.: US 7,182,782 B2
(45) Date of Patent: *Feb. 27, 2007

(54) SPINAL FUSION SYSTEM AND METHOD FOR FUSING SPINAL BONES

(75) Inventor: David Louis Kirschman, Dayton, OH (US)

(73) Assignee: X-spine Systems, Inc., Centerville, OH (US)

( * ) Notice: Subject to any disclaimer, the term of this patent is extended or adjusted under 35 U.S.C. 154(b) by 95 days.

This patent is subject to a terminal disclaimer.

(21) Appl. No.: 10/675,361

(22) Filed: Sep. 30, 2003

(65) Prior Publication Data

US 2005/0071006 A1    Mar. 31, 2005

(51) Int. Cl.
*A61F 2/44* (2006.01)
*A61B 17/56* (2006.01)

(52) U.S. Cl. .............................. 623/17.11; 623/17.16; 606/61

(58) Field of Classification Search ............. 623/17.11, 623/17.16; 606/61, 69
See application file for complete search history.

(56) References Cited

U.S. PATENT DOCUMENTS

| | | |
|---|---|---|
| 1,025,008 A | 4/1912 | Miner |
| 2,677,369 A | 5/1954 | Knowles |
| 3,848,601 A | 11/1974 | Ma et al. |
| 3,867,728 A | 2/1975 | Stubstad et al. |
| 4,157,715 A | 6/1979 | Westerhoff |
| 4,309,777 A | 1/1982 | Patil |
| 4,349,921 A | 9/1982 | Kuntz |
| 4,553,273 A | 11/1985 | Wu |
| 4,599,086 A | 7/1986 | Doty |
| 4,611,581 A | 9/1986 | Steffee |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buettner-Janz et al. |
| 4,834,757 A | 5/1989 | Brantigan |
| 4,878,915 A | 11/1989 | Brantigan |
| 4,988,349 A | 1/1991 | Pennig |
| 4,997,432 A | 3/1991 | Keller |
| 5,041,113 A | 8/1991 | Biedermann et al. |
| 5,084,049 A | 1/1992 | Asher et al. |
| 5,085,660 A | 2/1992 | Lin |
| 5,192,327 A | 3/1993 | Brantigan |

(Continued)

FOREIGN PATENT DOCUMENTS

CA        1292596        12/1991

(Continued)

*Primary Examiner*—Pedro Philogene
(74) *Attorney, Agent, or Firm*—Jacox, Meckstroth & Jenkins

(57) ABSTRACT

This invention relates to a spinal fusion system and method for use as a prosthetic implant. The system and method includes a housing dimensioned to be situated between adjacent spinal bones, such as adjacent vertebrae. The housing cooperates with the spinal bones to define a graft area for receiving graft material, which may be inserted anteriorly into the housing during a surgical operation such as a vertebrectomy or discectomy. A housing may have various features such as migration preventers to prevent the housing from migrating posteriorly towards a spinal column during or after insertion of the housing; a plurality of projections or crossbars may be removably inserted into the housing and can be used with a cover that permits the housing to "float" relative thereto.

172 Claims, 9 Drawing Sheets

U.S. PATENT DOCUMENTS

| | | |
|---|---|---|
| 5,246,443 A | 9/1993 | Mai |
| 5,261,911 A | 11/1993 | Carl |
| 5,290,312 A | 3/1994 | Kojlmoto et al. |
| 5,324,290 A | 6/1994 | Zdeblick et al. |
| 5,330,473 A | 7/1994 | Howland |
| 5,364,399 A | 11/1994 | Lowery et al. |
| 5,425,772 A | 6/1995 | Brantigan |
| 5,439,463 A | 8/1995 | Lin |
| 5,549,612 A | 8/1996 | Yapp et al. |
| 5,554,191 A | 9/1996 | Lahille et al. |
| 5,601,551 A | 2/1997 | Taylor et al. |
| 5,601,553 A | 2/1997 | Trebing et al. |
| 5,616,142 A | 4/1997 | Yuan et al. |
| 5,616,144 A | 4/1997 | Yapp et al. |
| 5,620,443 A | 4/1997 | Gertzbein et al. |
| 5,672,177 A | 9/1997 | Seldin |
| 5,681,310 A | 10/1997 | Yuan et al. |
| 5,681,311 A | 10/1997 | Foley et al. |
| 5,702,395 A | 12/1997 | Hopf |
| 5,713,899 A | 2/1998 | Marnay et al. |
| 5,713,900 A | 2/1998 | Benzel et al. |
| 5,716,415 A | 2/1998 | Steffee |
| 5,720,746 A | 2/1998 | Soubeiran |
| 5,776,196 A | 7/1998 | Matsuzaki et al. |
| 5,843,082 A | 12/1998 | Yuan et al. |
| 5,876,402 A | 3/1999 | Errico et al. |
| 5,888,228 A | 3/1999 | Knothe et al. |
| 5,904,683 A | 5/1999 | Pohndorf et al. |
| 5,925,047 A | 7/1999 | Errico et al. |
| 5,951,558 A | 9/1999 | Fiz |
| 5,954,722 A | 9/1999 | Bono |
| 6,030,389 A | 2/2000 | Wagner et al. |
| 6,066,175 A * | 5/2000 | Henderson et al. ...... 623/17.11 |
| 6,106,557 A | 8/2000 | Robioneck et al. |
| 6,136,002 A | 10/2000 | Shih et al. |
| 6,139,550 A | 10/2000 | Michelson |
| 6,152,927 A | 11/2000 | Farris et al. |
| 6,159,211 A | 12/2000 | Boriani et al. |
| 6,159,213 A | 12/2000 | Rogozinski |
| 6,159,245 A | 12/2000 | Meriwether et al. |
| 6,171,307 B1 | 1/2001 | Orlich |
| 6,193,721 B1 | 2/2001 | Michelson |
| D440,311 S | 4/2001 | Michelson |
| 6,224,602 B1 | 5/2001 | Hayes |
| 6,235,033 B1 | 5/2001 | Brace et al. |
| 6,235,034 B1 | 5/2001 | Bray |
| 6,235,059 B1 * | 5/2001 | Benezech et al. ........ 623/17.16 |
| 6,245,108 B1 | 6/2001 | Biscup |
| 6,258,089 B1 | 7/2001 | Campbell et al. |
| 6,261,586 B1 | 7/2001 | McKay |
| 6,264,655 B1 | 7/2001 | Pisharodi |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,328,738 B1 | 12/2001 | Suddaby |
| 6,368,351 B1 | 4/2002 | Glenn et al. |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,428,542 B1 | 8/2002 | Michelson |
| 6,432,106 B1 | 8/2002 | Fraser |
| 6,454,769 B2 | 9/2002 | Wagner et al. |
| 6,454,771 B1 | 9/2002 | Michelson |
| 6,485,517 B1 | 11/2002 | Michelson |
| 6,503,250 B2 | 1/2003 | Paul |
| 6,527,776 B1 | 3/2003 | Michelson |
| 6,533,786 B1 | 3/2003 | Needham et al. |
| 6,558,423 B1 | 5/2003 | Michelson |
| 6,558,424 B2 | 5/2003 | Thalgott |
| 6,569,201 B2 | 5/2003 | Moumene et al. |
| 6,575,975 B2 | 6/2003 | Brace et al. |
| 6,592,586 B1 | 7/2003 | Michelson |
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,626,907 B2 | 9/2003 | Campbell et al. |
| 6,652,525 B1 | 11/2003 | Assaker et al. |
| 6,669,700 B1 | 12/2003 | Farris et al. |
| 6,676,703 B2 | 1/2004 | Biscup |
| 6,679,883 B2 | 1/2004 | Hawkes et al. |
| 6,699,249 B2 | 3/2004 | Schläpfer et al. |
| 6,712,818 B1 | 3/2004 | Michelson |
| 6,755,833 B1 | 6/2004 | Paul et al. |
| 6,776,798 B2 | 8/2004 | Camino et al. |
| 6,837,905 B1 * | 1/2005 | Lieberman ............... 623/17.16 |
| 6,926,737 B2 * | 8/2005 | Jackson ................... 623/17.16 |
| 2002/0045898 A1 | 4/2002 | Fried et al. |
| 2002/0058939 A1 | 5/2002 | Wagner et al. |
| 2002/0120273 A1 | 8/2002 | Needham et al. |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0045880 A1 | 3/2003 | Michelson |
| 2003/0060828 A1 | 3/2003 | Michelson |
| 2003/0078668 A1 | 4/2003 | Michelson |
| 2003/0105462 A1 | 6/2003 | Haider |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127897 A1 | 7/2004 | Freid et al. |
| 2004/0127903 A1 | 7/2004 | Schlapfer et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMaurc et al. |
| 2004/0193271 A1 | 9/2004 | Fraser et al. |
| 2004/0210313 A1 | 10/2004 | Michelson |
| 2004/0230309 A1 | 11/2004 | DiMauro et al. |
| 2005/0038513 A1 | 2/2005 | Michelson |

FOREIGN PATENT DOCUMENTS

| | | |
|---|---|---|
| CA | 2133276 | 2/1999 |
| CA | 2383634 | 8/2001 |
| EP | 0179695 | 4/1986 |
| EP | 0307241 | 12/1992 |
| EP | 1437105 | 7/2004 |
| GB | 0401362.9 | 1/2004 |
| WO | WO 8909035 | 10/1989 |
| WO | WO 97/20526 | 6/1997 |

* cited by examiner

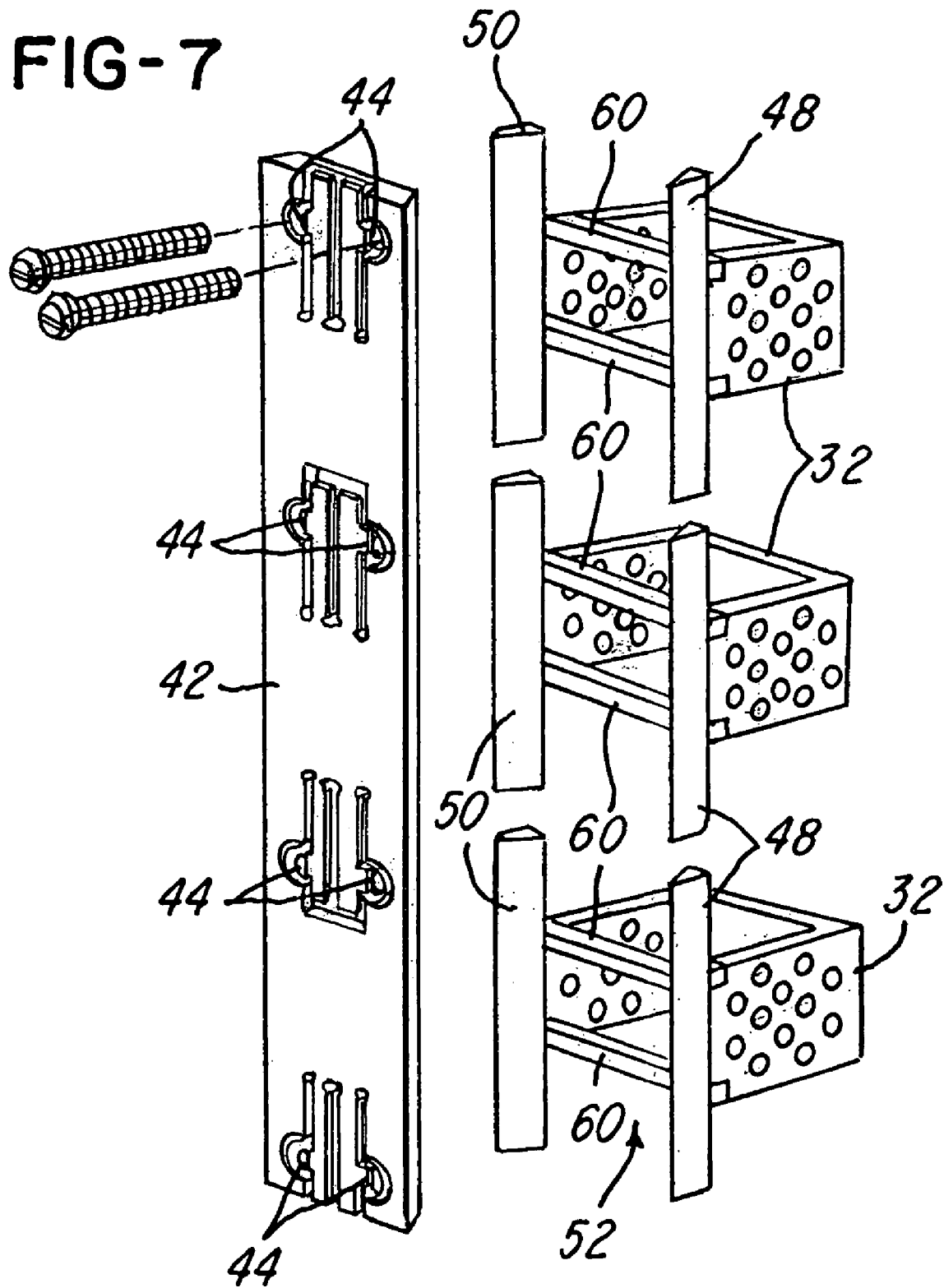

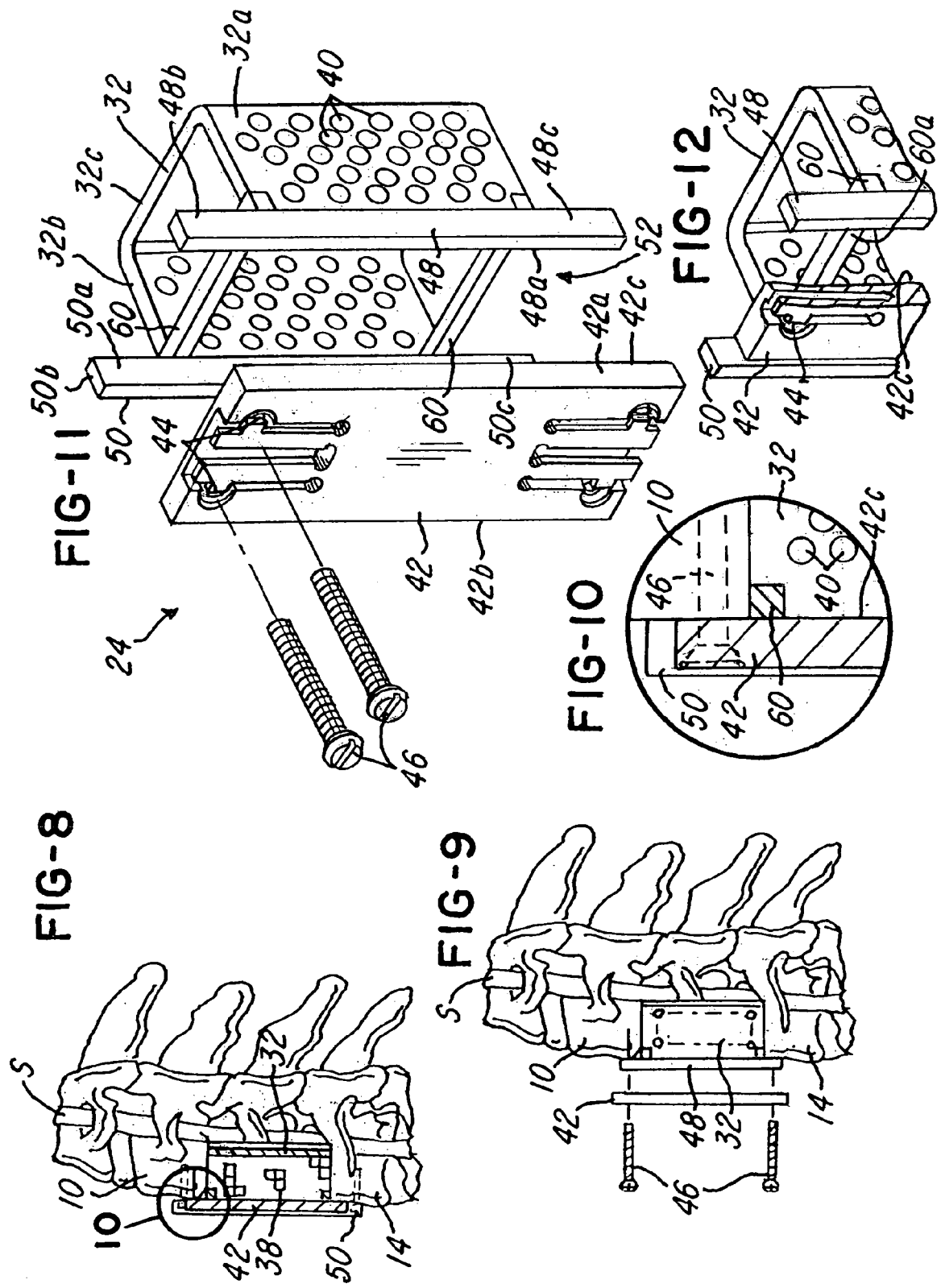

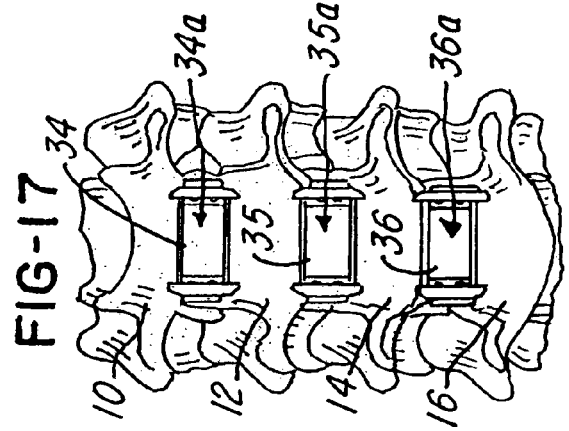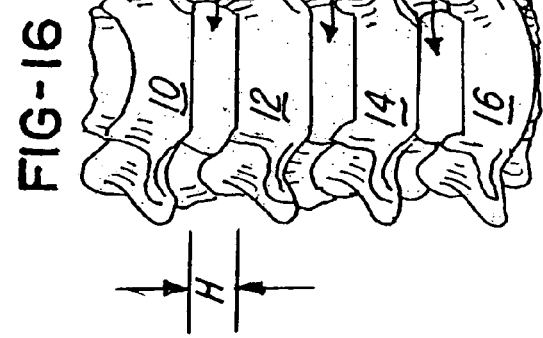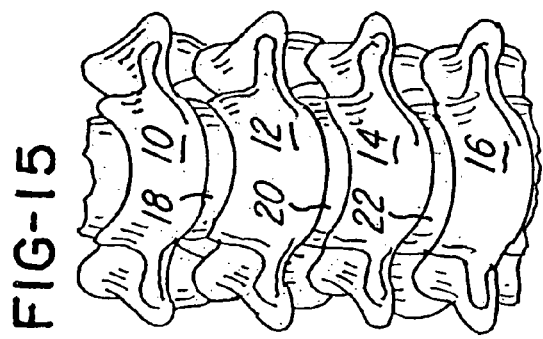
FIG-15  FIG-16  FIG-17
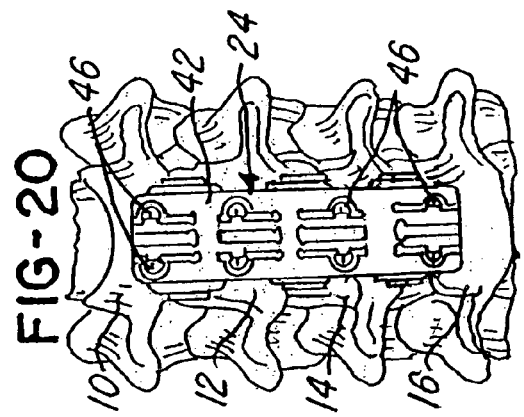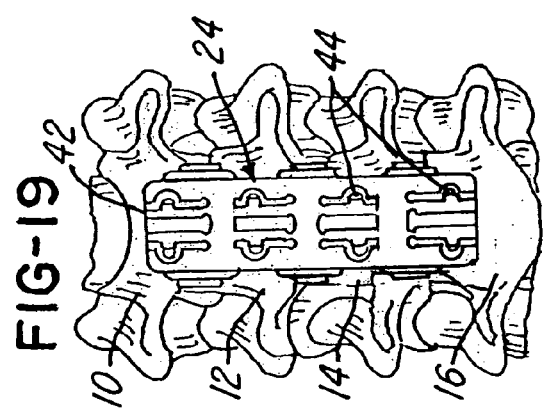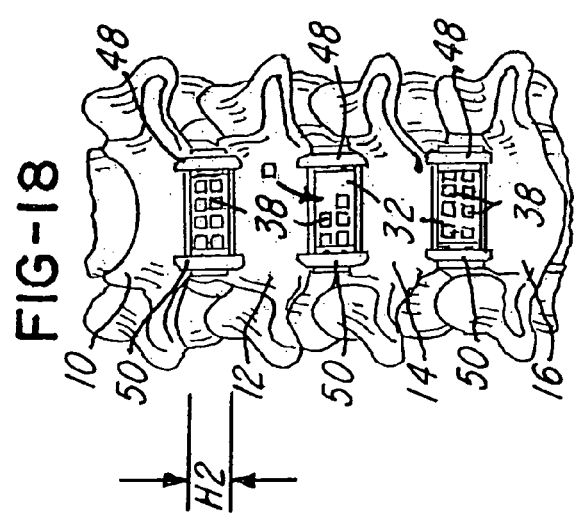
FIG-18  FIG-19  FIG-20

SPINAL FUSION SYSTEM AND METHOD FOR FUSING SPINAL BONES

BACKGROUND OF THE INVENTION

1. Field of the Invention

This invention relates to a veritable prosthetic system and device and a method for implanting the device and, more particularly, to a spinal fusion system and method for fusing spinal bones.

2. Description of the Related Art

Many types of prosthetic devices have been proposed in the past. For example, U.S. Pat. No. 5,192,327 to Brantagan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 5,192,327; 5,261,911; 5,713,899; 5,776,196; 6,136,002; 6,159,245; 6,224,602; 6,258,089; 6,261,586; 6,264,655; 6,306,136; 6,328,738 and 6,592,586. Some or all of these devices have improved the success rate and have simplified the surgical techniques in inter-body veritable fusion.

Among some of the problems associated with the prior art devices is that after the device is inserted into a patient during a surgical procedure, there was a possibility of retropulsion of the inter-body device and graft material into the spinal cord or other neurological element.

Another problem with the prior art devices is that grafting material, which was inserted into the devices during the surgical procedure, could not easily be inserted from an anterior direction.

Moreover, in some of the prior art devices, the cover, if any, was typically fastened directly to the device and to spinal bones, which prevented the cover from being capable of moving relative to the device. In addition, in devices that used a cover, the cover did not function to both retain the grafting material in the device and simultaneously fix the spinal bones relative to each other.

What is needed, therefore, is a system and method which facilitates overcoming one or more of the aforementioned problems as well as other problems and to provide a device that has unique features that will facilitate reducing the risk associated with neurological surgeries and advance the present state of the art.

SUMMARY OF THE INVENTION

It is, therefore, one object of the invention to provide a spinal fusion system and method which utilizes a housing that can be inserted, but comprises features which, for example, enables the device to float relative to a cover, facilitates retaining any graft material within the device, facilitates fixing a relative relation among or between spinal bones, facilitates providing a cover for covering one or multiple devices, and/or includes locking features that facilitates preventing the screws which secure the cover to the spinal bones from the retracting.

In one embodiment, the invention comprises a spinal fusion system for use as a prosthetic implant comprising a housing dimensioned to be situated between adjacent spinal bones, the housing defining a graft area the housing comprising at least one wall that defines an opening after the housing is situated between the adjacent spinal bones to permit in-situ loading of graft material.

In another embodiment, the invention comprises a spinal bones fusing system comprising a housing for situating between a first spinal bones and a second spinal bones the housing being generally U-shaped and cooperating with the first and second spinal bones to define an opening that opens into a graft area for receiving graft material.

In another embodiment, the invention comprises a method for fusing spinal bones together, comprising the steps of situating a cage in a graft area between spinal bones, the cage cooperating with the spinal bones to define an anterior opening for introducing graft material into the graft area situating graft material through the anterior opening and into the graft area; and covering the anterior opening with a cover.

In still another embodiment, the invention comprises an implant for facilitating grafting spinal bones together, comprising a housing for situating between the spinal bones, the housing cooperating with the spinal bones to define a graft area and an opening for introducing graft material into the graft opening; and a cover for securing to the spinal bones, the cover covering the opening after the graft material is situated is fixed to the spinal bones.

And yet another embodiment, the invention comprises, a method for fusing spinal bones together, comprising the steps of providing a housing for situating between spinal bones, the housing cooperating with the spinal bones to define an opening for introducing graft material into the graft area after the housing and enabling the graft material to be introduced through the opening and into the graft area after the housing is situated between the spinal bones.

In another embodiment, the invention comprises a prosthetic implant plate comprising a generally planar member; and an integral lock for preventing withdrawal of at least one screw after the at least one screw is screwed into a spinal bone.

In another embodiment, the invention comprises a spinal fusion system for use as a prosthetic implant comprising a housing dimensioned to be situated between adjacent spinal bones, the housing defining a graft area for receiving a graft or graft-like material for generating a fusion between the adjacent spinal bones, the housing comprising at least one wall that defines an opening after the housing is situated between the adjacent spinal bones to permit post-placement loading of graft material.

These and other objects and advantages of the invention will be apparent from the following description, the accompanying drawing and the appended claims.

BRIEF DESCRIPTION OF THE DRAWINGS

FIG. 7 is an exploded view of the device shown in FIG. 6, illustrating a plurality of housings and a single cover for use with covering the plurality of housings;

FIG. 8 is partial side view illustrating an elongated housing and cover used during a vertebrectomy procedure;

FIG. 9 is a partial side view of the spinal column illustrated in FIG. 8 showing the elongated housing situated between adjacent spinal bones in a single cover to be affixed to those spinal bones;

FIG. 10 is an exploded view of the circle area shown in FIG. 8;

FIG. 11 is an exploded view of the elongated housing illustrated in FIGS. 8 and 9 and the cover and screws associated therewith;

FIG. 12 is a partial fragmentary view of the cover and housing after the cover has been situated between a pair of rails associated with the housing;

FIG. 15 is a partial anterior side view of a human spine illustrating the discs between various spinal bones;

FIG. 16 is a partial anterior view of the spinal column shown in FIG. 1 illustrating several of the discs removed, such as by surgical procedure;

FIG. 17 is a partial anterior view of the human spine with the housings according to one embodiment of the invention situated therein;

FIG. 18 is a partial anterior view of the human spinal column illustrating graft material being inserted anteriorly into the housing;

FIG. 19 is a partial exploded anterior view of the embodiment shown in FIG. 1–4 illustrating a cover and a plurality of screws for securing the cover to the spinal column;

FIG. 20 is a anterior view similar to FIG. 5 illustrating the cover mounted to the spinal column;

DETAILED DESCRIPTION OF PREFERRED EMBODIMENTS

Figure 2:
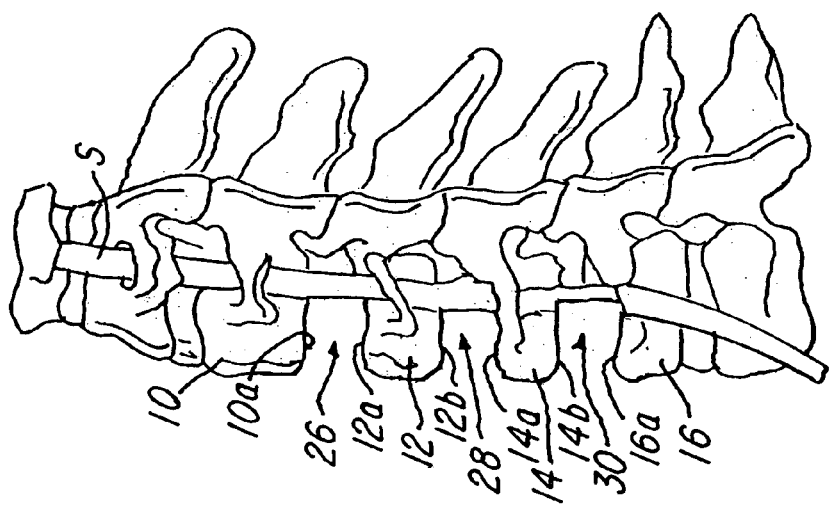
FIG. 2 is a partial side view of the spinal column shown in FIG. 1 illustrating several of the discs removed, for example, after surgical procedure.
Figure 1:
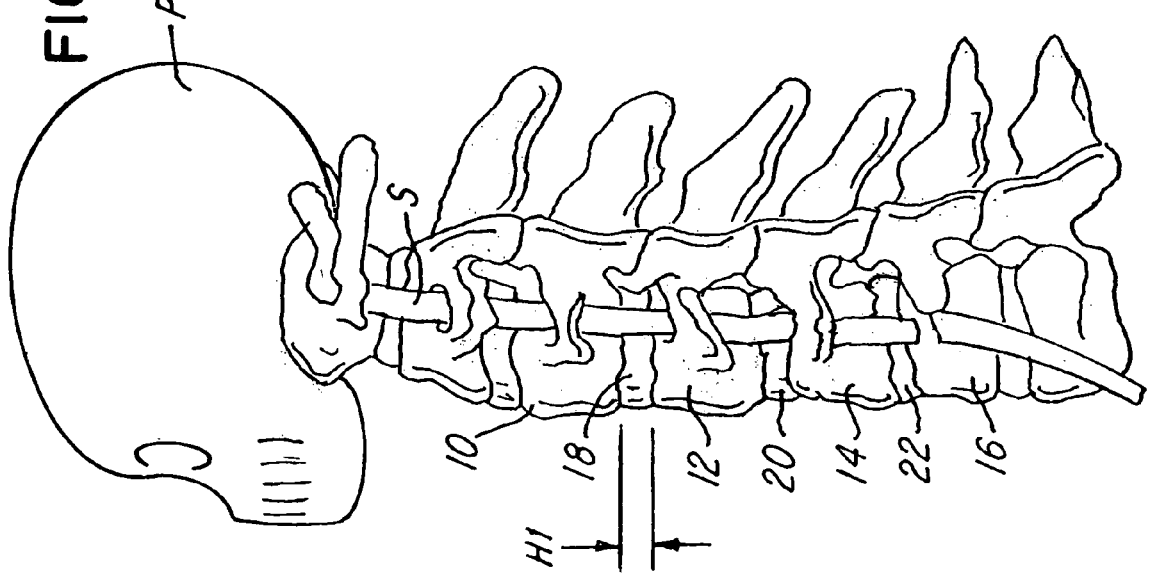
FIG. 1 is a partial side view of a human spine illustrating anteriorly discs between various spinal bones.
Figure 13:
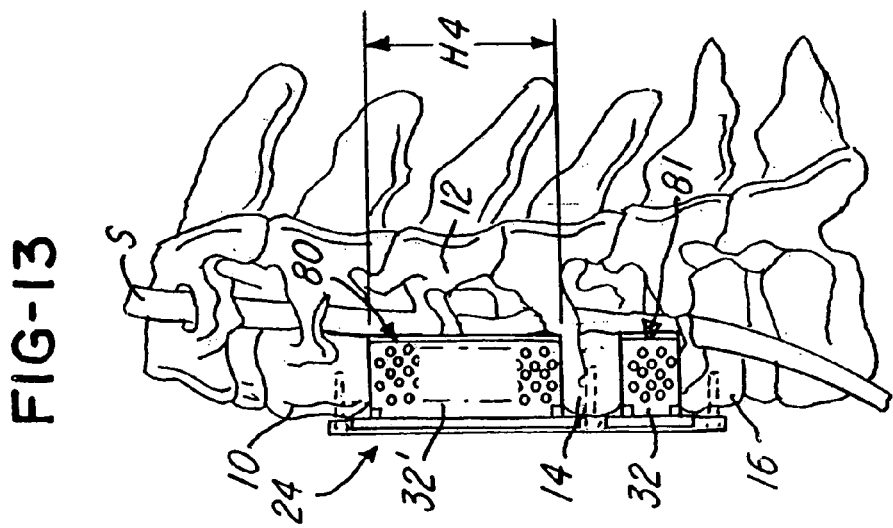
FIG. 13 illustrates a partial side view of an embodiment showing a plurality of housings of different sizes used with a single cover.

Referring now to FIG. 1, a partial side view of a patient or person P is shown having a spinal column S and a plurality of spinal bones, such as vertebrae, 10, 12, 14 and 16. Note that a disc, such as discs 18, 20 and 22 in FIG. 1, is located between adjacent pairs of spinal bones (e.g., between bones 10 and 12, 12 and 14, and 14 and 16). During a spinal fusion procedure, such as a discectomy, the discs 18, 20 and 22 may be removed so that adjacent vertebrae may be fused together FIG. 2 illustrates a fragmentary view of the spinal column S shown in FIG. 1, with the discs 18, 20 and 22 removed. It should also be understood that during another surgical procedure, such as a vertebrectomy, it may be desired to remove part or all of one of the spinal bones 10–16, as illustrated in FIG. 13. In this type of neurological procedure, it may also be desired to fuse adjacent spinal bones together for reasons that are conventionally known. This invention provides means for facilitating and performing such procedures. For ease of illustration, FIGS. 15–20 provide corresponding anterior views to the side views shown in FIGS. 1–6, respectively.

In the embodiment being described, a spinal fusion system 24 is provided for use as a prosthetic implant during a neurological procedure such as the aforementioned vertebrectomy or discectomy. In general, after the discs 18, 20 and 22 (FIG. 1) are removed, as illustrated in FIG. 2, a plurality of receiving areas 26, 28 and 30 (FIGS. 2 and 17) are defined by the areas between the surfaces of adjacent spinal bones 10, 12, 14 and 16. As illustrated in FIG. 2, the area 26 is bounded in part by the surface 10a of spinal bone 10 and surface 12a of spinal bone 12. Likewise, area 28 is partially bounded by surface 12b of spinal bone 12 and surface 14a of spinal bone 14, and area 30 is bounded by surface 14b of spinal bone 14 and surface 16a of spinal bone 16.

Figure 3:
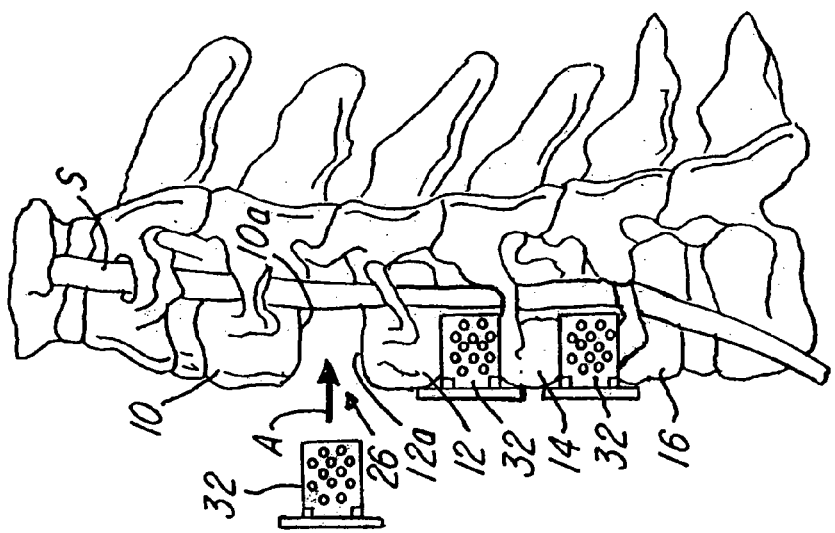
FIG. 3 is a partial side view of the human spine with the housings according to one embodiment of the invention situated therein.
Figure 4:
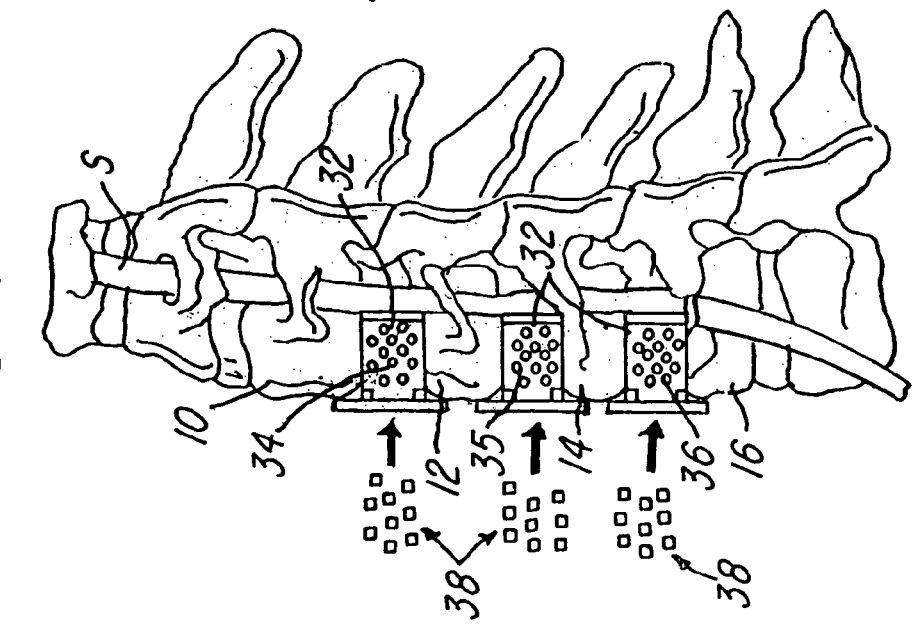
FIG. 4 is a partial side view of the human spinal column illustrating graft material being inserted anteriorly into the housing.

As illustrated in FIGS. 3–7 and 11 and as will be described in more detail later herein, the spinal fusion system 24 comprises a housing 32 dimensioned to be situated or received between adjacent spinal bones, such as bones 10 and 12. A housing 32 is situated in each of the plurality of receiving areas 26, 28 and 30, as illustrated in FIGS. 3–4. Each housing 32 cooperates with adjacent spinal bones to define a graft area, such as areas 34, 35 and 36 in the view illustrated in FIG. 17, for receiving graft material 38 (FIGS. 4 and 18). As illustrated in FIGS. 4 and 18, the graft material 38 is situated in the areas 34, 35 and 36 after placement of the housing 32.

As illustrated in FIG. 11, the housing 32 is generally U-shaped as shown. In the embodiment being described, the housing 32 comprises a well 33 defining multiple sides and comprising a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired. Note that the housing 32 comprises a first wall 32a, a second wall 32b and a third wall 32c joining the first wall 32a and the second wall 32b. One or more of the walls 32a–32c may comprise a plurality of holes or apertures 40 which facilitate the fusing process. The apertures 40 also permit visualization of graft material 30 on x-rays.

As mentioned later herein, the predetermined shape defined by the spinal fusion system 24 may provide a fused multi-sided plug of fusion material 32 having a height H (FIGS. 14 and 16) of at least two millimeters, but typically less than approximately 180 millimeters. This height H may vary depending on the vertical size or height H (as viewed in FIG. 16) of the areas 26–30 to be filled. For example, in the area 26 illustrated in FIGS. 2, 14 and 16, the height H of the area 26 generally corresponds to a height H1 (FIG. 1) of a disc, such as disc 18. Thus, the fusion material 38 (FIG. 18) would resultantly have a fused height H2 (FIG. 18) that generally corresponds to the height H (FIG. 16) and height H1 (FIG. 1). If, for example, a housing 32 having a longer height is required, such as height H3 in FIG. 14 and height H4 in FIG. 13, such as in the event of a vertebrectomy, then the fusion system 24 and housing 32 will define a height that generally corresponds to the dimension or height H (FIG. 9) to be traversed. Thus, it should be understood that the dimensions of the generally U-shaped housing 32 of the spinal fusion system 24 is selected depending on the size of the area 26–30 to be filled and the environment or application in which the spinal fusion system 24 is used. In general, the width and depth of the housing 32 will be approximately 9–20 millimeters and 7–20 millimeters, respectively.

Figure 6:
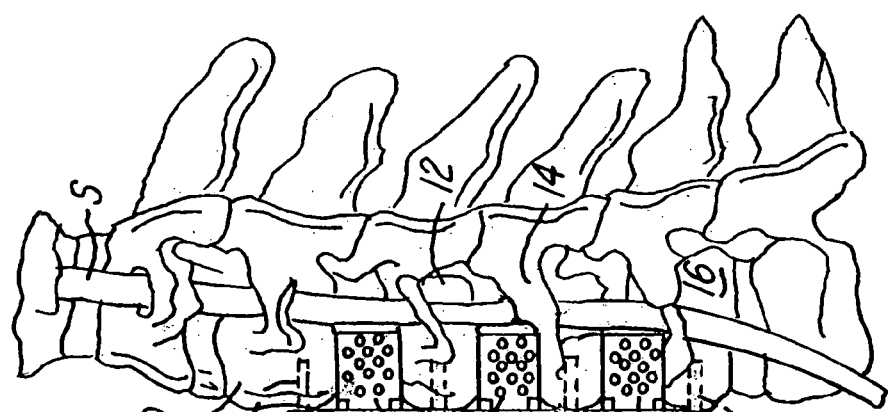
FIG. 6 is a side view similar to FIG. 5 illustrating after the cover has been mounted to the spinal column.
Figure 5:
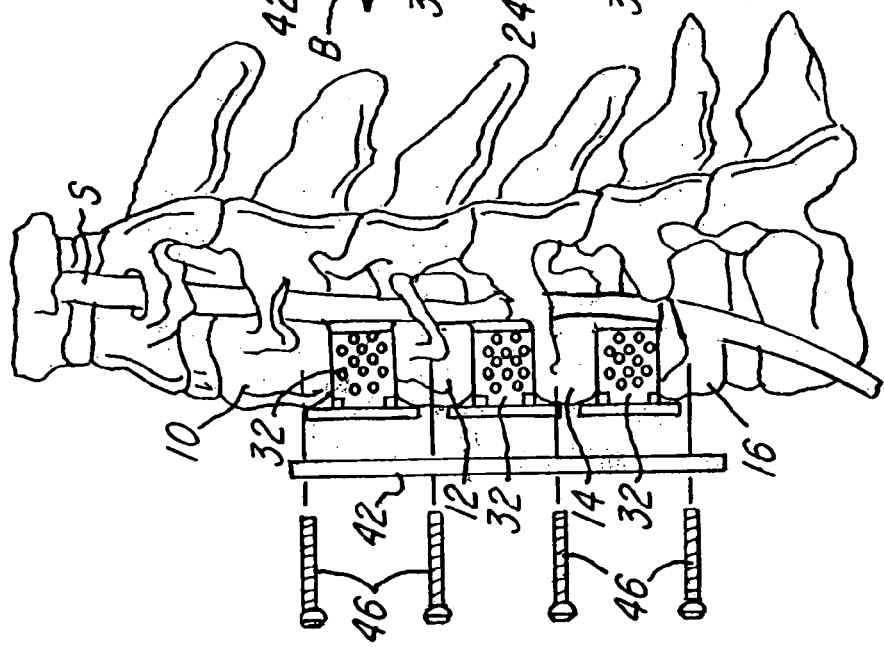
FIG. 5 is a partial exploded side view of the embodiment shown in FIG. 1–4 illustrating a cover and a plurality of screws which will secure the cover to the spinal column.

As illustrated in FIGS. 5–7, 11, 14 and 21–22, the spinal fusion system 24 further comprises a cover 42 comprising a plurality of apertures 44 that receive a plurality of screws 46, respectively, which are screwed directly into the spinal bones 10 and 16, as illustrated, for example, in FIGS. 5–6.

Figure 23:
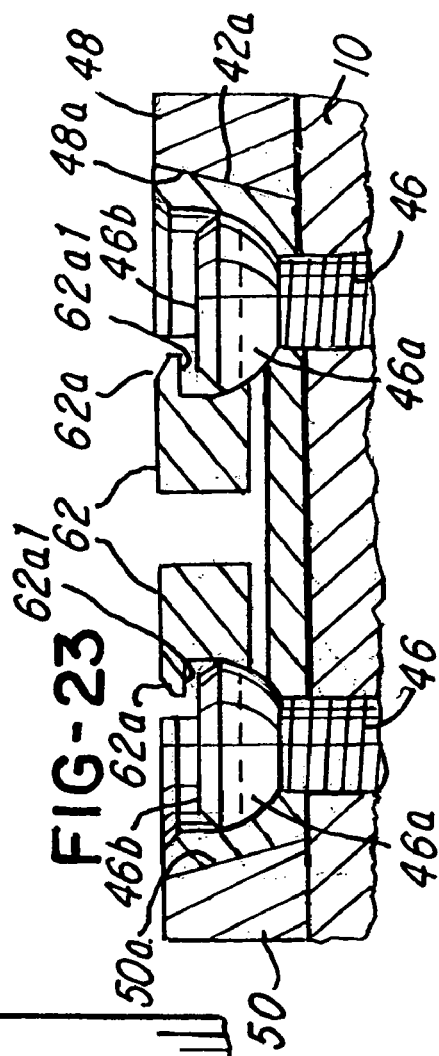
FIG. 23 is a fragmentary sectional view of the embodiment shown in FIG. 22 illustrating various features of the locking mechanism.

As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel 52, the sides 42a and 42b become associated with the sides 48a and 50a. It should be understood that the cover 42 is not permanently secured to the housing 32 after it is received in channel area 52. This feature permits the housing 32 to migrate or float relative to the cover 42 even after the cover 42 is fixed to one or more of the spinal bones 10–16 as illustrated in FIGS. 6 and 20. As illustrated in FIG. 23, the edges 42a and 42b of cover 42 and sides 48a and 50a may be beveled and complementary to facilitate locating and mating engagement between the cover 42 and housing 32.

As illustrated in FIGS. 3–6 and 16–20, after the graft material 38 is placed in the housing 32 and the graft areas 35–36 (FIG. 17) defined by the housing 32 and adjacent spinal bones, then the cover 42 is situated between the walls or rails 48 and 50, as illustrated in FIGS. 6 and 19. The screws 46 may then be used to secure the cover 42 to one or more of the spinal bones 10–16 as illustrated in FIGS. 6 and 20. It should be understood that a feature of the invention is that the cover 42 facilitates aligning the housings 32 in a substantially co-lineal or relatively aligned position relative to each other and to the spinal bones 10–16, as illustrated in FIGS. 6, 19 and 20. In the setting of multiple level discectomy, the floating cover 42 allows limited, controlled settling of the cages or housings 32 in the vertical plane with respect to the cover 42. As illustrated in FIGS. 6, 8, 10 and 20, the cover 42 also provides means for providing a mechanical fixation of the adjacent spinal bones 10–16 relative to each other. Thus, while the housing 32 cooperates with adjacent spinal bones, such as spinal bones 10 and 12, to define a graft receiving area 34, the cover is multi-functional in that it not only covers the opening of any graft areas, such as area 34 (FIG. 17), but it also secures and retains the spinal bones 10–16 in a fixed spatial relationship relative to each other and relative to the housings 32. It should also be understood that the cover 42 may be fixed to one or more of the spinal bones 10–16 as may be desired to accomplish either of the aforementioned functions.

As illustrated in FIG. 11, note that the walls 48 and 50 further define projections 48b, 48c, 50b and 50c as shown. As illustrated in FIGS. 3–6 and 17–20, the projections 48b, 48c, 50b and 50c provide a plurality of migration preventers for preventing the housing 32 from migrating posteriorly in the direction of arrow A (FIG. 3) toward the spinal cord S or other neurological elements after the housing 32 is situated between the adjacent spinal bones 10–16 as illustrated. Further, the migration preventers 48b, 48c, 50b and 50c enable a surgeon to locate each housing 32 between adjacent spinal bones, such as spinal bones 10–16 in FIG. 1, and move the housing 32 in the direction of arrow A in FIG. 3 until the migration preventers 48b, 48c, 50b and 50c engage the surface 10a of spinal bone 10 and migration preventers 48b, 48c, 50b and 50c engage the surface 12a of spinal bone 12. As illustrated in FIG. 3, after the housings 32 are situated between the spinal bones 10–16 as shown, the migration preventers 48b, 48c, 50b and 50c facilitate preventing the wall 32c from being over-inserted by the surgeon or from being over-inserted to a point where it engages the spinal cord S or other neurological elements.

Figure 26:
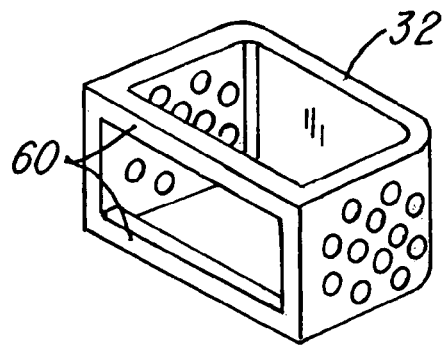
FIG. 26 is a view of another embodiment of the invention showing the crossbars integrally formed in the housing and without migration preventers.

The spinal fusion system 24 further comprises at least one migration stop or crossbar 60 as illustrated in FIGS. 11, 12, 29 and 30. The crossbar 60 may be either integrally formed in housing 32, as shown in FIG. 26, or separate as illustrated in FIGS. 7, 11, 12, 14, 29 and 30, for example. As illustrated in the exploded view in FIGS. 10 and 11, the surface 60a of crossbar 60 engages and cooperates with surface 42c of cover 42 to prevent anterior migration in the direction of arrow B). Thus, the spinal fusion system 24 of the embodiment being described provides means for preventing insertion of the housing 32 to a point where it might engage the spinal cord S (FIG. 3) or other neurological elements, such as dura mater, thecal sac, and also means for facilitating prevention of migration of the housing 32 in an anterior direction or in the direction of arrow B in FIG. 10 after the housing 32 is situated as described herein and the cover 42 is mounted to one or more of the spinal bones 10–16.

Figure 29:
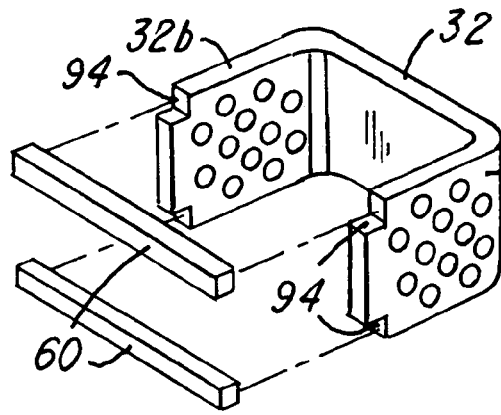
FIG. 29 is another view of the housing illustrating a plurality of removable crossbars without any migration preventers.
Figure 30:
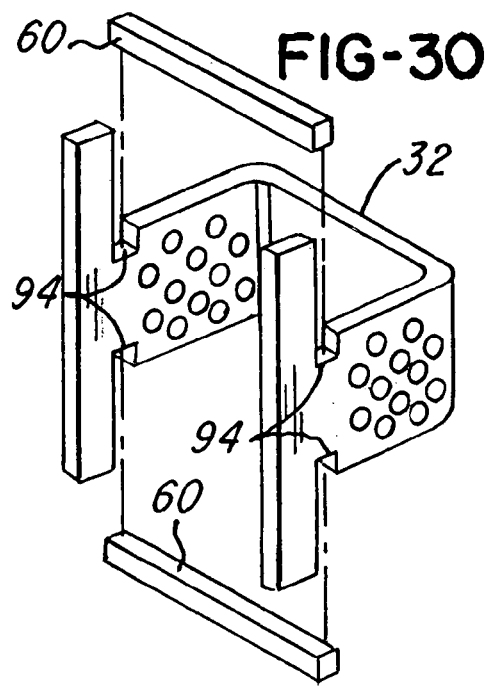
FIG. 30 illustrates another embodiment of the invention, similar to the devices illustrated earlier relative to FIG. 1–20 showing details of the cross bars and notches for receiving them.

It should be understood that a plurality of the migration stops or cross bars 60 may be used alone or in combination with the migration preventers 48b, 48c, 50b and 50c. It should be understood that the stops 60 could be detachable, as shown in FIG. 26, or they could be integrally formed in housing 32 (as shown in FIG. 26). Also, these cross bars 60 may be removably received in the notched receiving areas 94 (FIGS. 29–30). For example, in anatomy that provided limited space, the surgeon may elect not to use a housing with cross bars 60 or use a housing that does not have integrally formed cross bars.

The system 24 further comprises a system or means for preventing retraction or back out of the screws 46 after they are screwed into the spinal bones 10–16 in order to secure the cover 42 thereto. The spinal fusion system 24 of the present invention may be used with conventional screw lock devices or with a unique locking mechanism and system, which will now be described relative to FIGS. 21–23.

Figure 22:
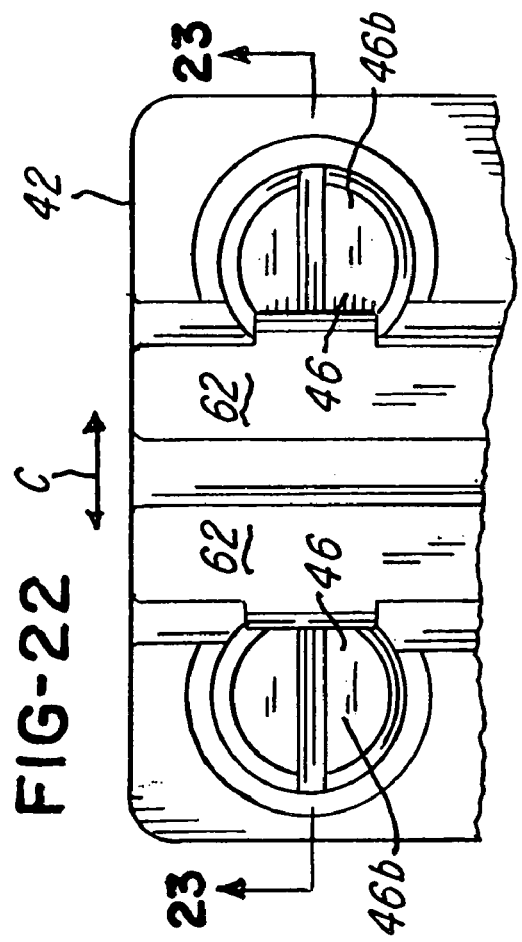
FIG. 22 is another fragmentary view of the cover after the screws are mounted and the locking mechanism retains the screws therein.
Figure 21:
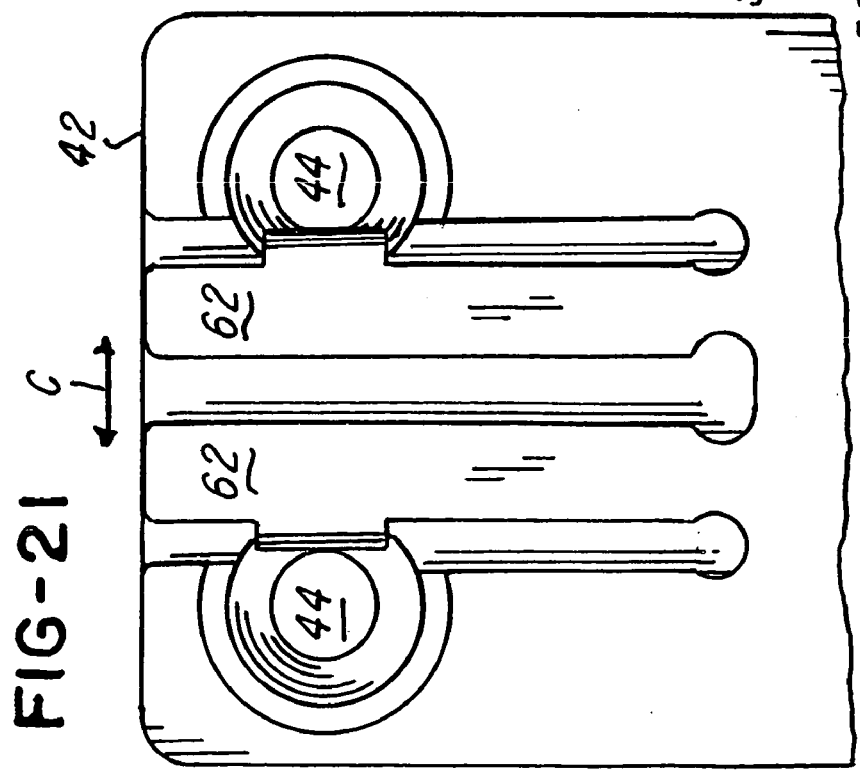
FIG. 21 is a fragmentary view illustrating various features of the cover.

As illustrated in FIGS. 21–23, the spinal fusion system 24 and, more particularly, cover 42 may be provided with at least one or a plurality of resilient detents 62 which are generally L-shaped as shown and are resilient so that they can move laterally in the direction of double arrow C in FIGS. 21–22 towards and away from a home position (FIG. 21) to permit the screws 46 first received in the apertures 44, and, second, locked into the cover 42. Thereafter, the screws 46 may be screwed into a spinal bone, such as spinal bone 10, and when a screw head 46a of the screw 46 engages a detent portion 62a of the resilient lock 62, the resilient lock 62 moves in a direction away from the apertures 44 until the screw head 46a clears the portion 62a. After a top surface 46b of the screw head 46a has cleared the bottom surface 62a1 (as viewed in FIG. 23) of portion 62a, the resilient lock 62 moves back toward aperture 44 to the home position until the portion 62a and surface 62a1 are operatively positioned over surface 46b of screw 46, thereby retaining and preventing the screws 46 from backing out of the cover 42 and thereby preventing the screws 46 from backing out of the spinal bone 10.

In the embodiment being described, the components of the spinal fusion system 24, such as the housing 32, first channel wall portion 48 and second channel wall portion 50, crossbar 60, cover 42 and screws 46 may be made of any desired composition or material such as a polymer, composite polymer, titanium, stainless steel, carbon fiber or other suitable material.

A method for fusing spinal bones together will now be described relative to FIG. 22. It should be understood that this procedure may be used during a vertebrectomy or discectomy or other neurological procedure during which it is desired to fuse spinal bones together. For ease of illustration, the embodiment will be described as used during a discectomy procedure during which the discs 18–22 (FIG. 1) are removed so that spinal bones 10–16 may be fused together. The procedure begins by situating a patient P on an operating table (not shown) and providing an appropriate incision as conventionally known to expose the spinal bones such as the bones 10–16 illustrated in the side view shown in FIG. 1 and in the anterior view illustrated in FIG. 15. (Block 70 in FIG. 22). At Block 72, the vertebrae or discs, such as discs 18–22 in FIGS. 1 and 15, are surgically removed revealing the areas 26–30 in FIGS. 2 and 16. At Block 74, the housings 32 are inserted in the direction of arrow A (FIG. 3) into the areas 26, 28 and 30 until the migration preventers 40b, 48c, 50c and 50d engage the surfaces of the spinal bones 10–16, such as the surfaces 10a and 12a illustrated in FIG. 3. (Block 74 in FIG. 22). As mentioned earlier herein, the migration preventers facilitate preventing inserting the housing 32 to a point which would cause the wall 32c to engage the spinal column S.

As illustrated in FIGS. 3 and 17, the housing 32 cooperates with adjacent spinal bones, such as bones 10 and 12 to define the graft receiving area or cavity 34 in which the graft material 38 (FIG. 4) may be inserted. As mentioned earlier herein, these graft areas 34–36 may comprise a shape which is generally rectangular, as defined by the shape of the housing 32, but it could comprise another shape by simply providing a housing 32 having a different predetermined shape. Thus, the housing 32 may be provided in a circular or arcuate shape in which case the graft area 34 would define a generally circular or arcuate area which would cause the graft material to form a similar shape. Other curved or multi-sided shapes may be defined by providing an appropriately or correspondingly shaped housing 32, depending on the selected or desired shape that the physician would like the fused graft material 38 to assume after it has fused to the adjacent spinal bones.

At Block 76, the graft material 48 is inserted and at Block 78, the cover 42 is situated in the slot or area 52 defined by the walls 48 and 50. As mentioned earlier herein, the cover 42 facilitates covering the openings, such as openings 34a and 36a of the graft areas 34 and 36, respectively. The surgeon secures the cover 42 to one or more of the bones, as illustrated in FIGS. 5–6 and 19–20 and then closes the patient (Block 80).

Figure 24:
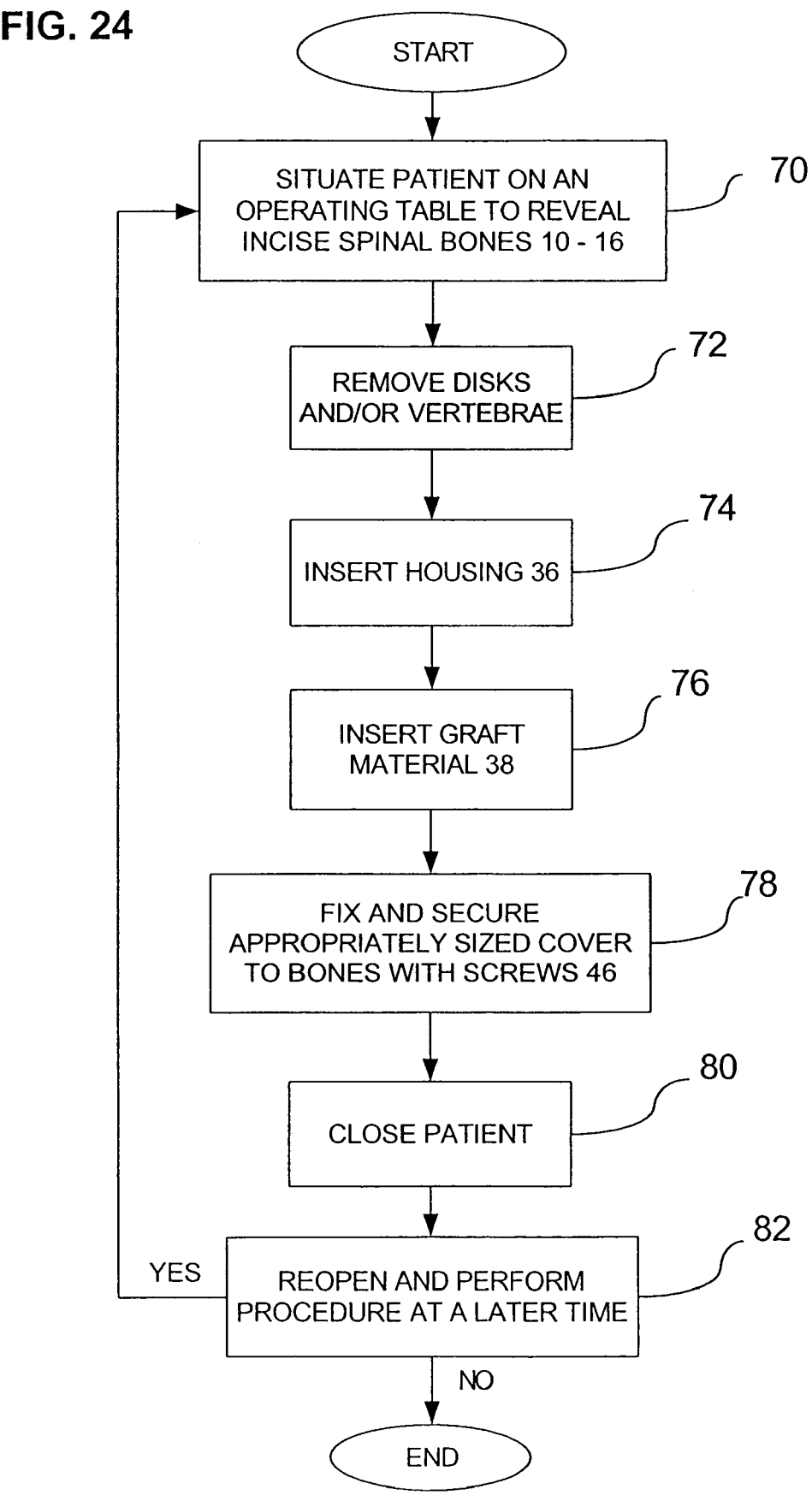
FIG. 24 is a schematic view of a process or method in accordance with an embodiment of the invention.

Again, and as mentioned earlier, a feature of the invention is that it provides a fixing system for fixing the location of the bones 12–16 relative to each other. Simultaneously, the system 24 permits the housing 32 to "float" between adjacent bones, such as bones 10 and 12 in FIGS. 3 and 6. This is advantageous for reasons mentioned earlier herein. Another advantage on this feature of the invention is that if it is necessary to operate on the same patient at a later time (Block 82 in FIG. 24) and, for example, add one or more housings 32 in order to fuse other spinal bones together, then the cover 42 can simply be removed at a later time, another discectomy or vertebrectomy performed and another housing 32 inserted. Another cover 42, or perhaps a second cover may then be used to seal the additional housing 32 after it is situated in the manner described herein. Thus, this invention provides a system and method which is flexible and will permit the addition or insertion of additional housings 32 of the same or different sizes during a second operating procedure as illustrated in Block 82.

Figure 14:
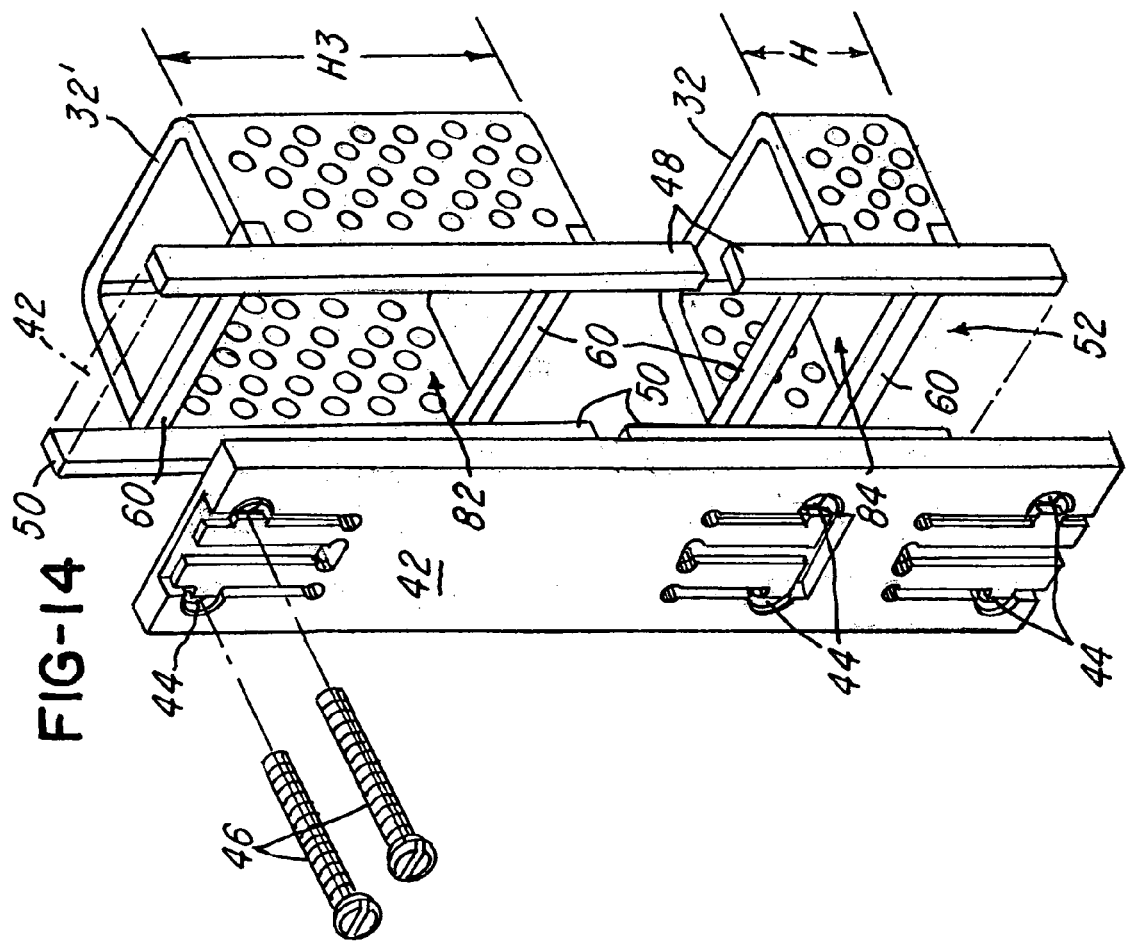
FIG. 14 is an exploded view of the housings and cover illustrated in FIG. 13.

FIGS. 1–8 and 15–20 illustrate the general procedure and use of the invention in an illustrative discectomy wherein three discs are removed, replaced with housing 32, and graft material 38 inserted as described and cover 42 situated and mounted as described herein. In the illustration shown in FIGS. 1–8 and 15–20, three discs 18–22 are removed and the spinal bones 12–16 are fused together using the system and method as shown and described. It should be appreciated, however, that this system and method may be used with fewer or more housings 32 and with one or a plurality of covers 42 as may be desired or required. For example, if only one of the discs 18–22 needed to be excised and only two of the spinal bones 10–16 fused together, then only one housing 32 and cover 42 may be necessary. Likewise, as mentioned earlier herein, the housings 32 may comprise a different dimension or different height H (FIG. 14) to span a greater area, such as the area H4 illustrated in FIGS. 13 and 14. For example, FIGS. 13 and 14 illustrate a vertebrectomy wherein the spinal bone 12 has been removed along with the disc between spinal bones 14 and 16. This provides areas 80 and 81 in which an elongated housing 32', such as the housing 32' illustrated in FIG. 14 may be inserted. After the housings 32 and 32' are inserted between the spinal bones 10–14 and 14–16 as shown in FIG. 13, graft areas 82 and 84 are provided for receiving the graft material 38. As illustrated in FIG. 13, the cover 42 would have a corresponding elongated shape for fixing the bones 10 and 14 together and for covering both openings 82 and 84 or housings 32 and 32'.

It is also anticipated that the invention may be used in a multitude of procedures, such as a vertebrectomy (FIGS. 8 and 9), discectomy (FIGS. 1–7, 13–20, or even a combination of a vertebrectomy and discectomy as illustrated in FIGS. 13–14. As mentioned and described earlier herein, a combination of different sizes of housings 32 and covers 42 may be used as shown. Although it is preferred that a single cover 42 be used, it may be desired in some applications to use multiple covers 42, such as where the removed discs are not adjacent.

In the illustrations being described, the housings 32 comprise the crossbar 60 which cooperate with the cover 42 to prevent anterior migration of the housing after the screws 46 are secured to the spinal bones as illustrated in FIGS. 6, 9 and 13.

Figure 25:
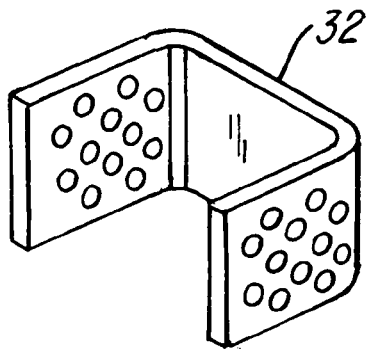
FIG. 25 illustrates another embodiment of the invention without crossbars or migration preventers.

FIGS. 25–30 illustrate other embodiments of the invention. In FIG. 25, a generally U-shaped housing 32 is provided without the walls 48 and 50 or crossbar 60. This embodiment may be useful. This may be useful if it were desired to insert housing 32 in local anatomy so that it could be loaded from the side or laterally, rather than anteriorly, as previously described.

In FIG. 26 a housing 32′′′ is provided with the crossbars 60, but without the walls 48 and 50. In this embodiment it may be useful to use such a housing design when the local anatomy provides limited space.

Figure 27:
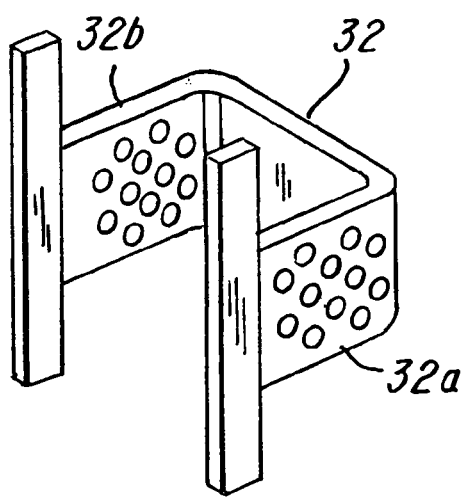
FIG. 27 is a view illustrating a plurality of migration preventers, without any crossbars.
Figure 28:
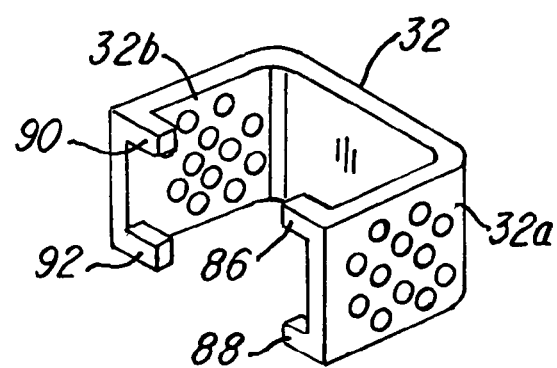
FIG. 28 is a view illustrating a housing with a plurality of projections which cooperate with the cover to prevent the housing from migrating anteriorly.

FIG. 27 illustrates yet another embodiment of the invention illustrating a housing 32 that is provided with a plurality of protrusion 86, 88, 90 and 92 that do not span completely between the walls 32*b* or 32*a* together but yet provide the protrusions 86–92 which will engage the cover 42 if the housing attempts to migrate anteriorly as described earlier herein. FIGS. 1–24, 29 and 30 show embodiments of the invention where the crossbars 60 are not integrally formed with the housing 32, but received in the notched areas 90 as shown. As mentioned earlier, the crossbars 60 may be separate or may be integrally provided with the housing 32. Providing detachable crossbars 60, such as is shown in the embodiments illustrated in FIGS. 25, 28 and 29, enable the walls 32*a* and 32*b* to flex towards and away from each other. The housing 32 may be provided with a malleable material in which case the surgeon can change the general U-shape of the housing 32 to accommodate the size or shape of the areas 34 and 36 (FIG. 17). In the embodiment described, housing 32 and cover 42 may be made of titanium, polymer or a bioresorbable material.

It should be understood that walls 48 and 50 may have notched areas (not shown) for receiving the cover 42, thereby eliminating the need for cross bars 60.

Advantageously, the various embodiments of the invention illustrated in FIG. 1, provide a system and method for inserting graft material 32 into a graft area 34 and 36 (FIG. 17) to fuse a plurality of bones such as bones 10–18 together. The system and method also provide means for fixing the bones 10–18 relative to each other, while permitting the housing 32 to cooperate with adjacent bones 10–18 to define a graft area 34 and 36 (FIG. 17) and to also float relative to the cover 42. The locking system illustrated in FIGS. 21–23 further facilitates providing a locking system that does not require the use of any tools, yet prevents back out of the screws 46.

While the apparatus and method described constitute preferred embodiments of this invention, it is to be understood that the invention is not limited to this precise apparatus and method, and that changes may be made in either without departing from the scope of the invention, which is defined in the appended claims.

What is claimed is:

1. A spinal fusion system for use as a prosthetic implant comprising:
   a housing dimensioned to be situated between adjacent spinal bones, said housing defining a graft area;
   said housing comprising at least one wall that defines an opening after said housing is situated between said adjacent spinal bones to permit in-situ loading of graft material;
   a cover for covering said opening to facilitate preventing anterior migration of said graft material; and
   said cover adapted to be secured to at least one of said adjacent spinal bones such that it permits said housing to migrate or float relative to said cover.

2. The spinal fusion system as recited in claim 1 wherein said housing is generally U-shaped.

3. The spinal fusion system as recited in claim 1 wherein said housing surrounds, said graft area and cooperates with said adjacent spinal bones to define a caged area comprising a predetermined shape and defining an anterior opening to permit said in-situ loading of said graft material.

4. The spinal fusion system as recited in claim 3 wherein said predetermined shape causes said graft material to be formed into a multi-sided fused coupling between said adjacent spinal bones.

5. The spinal fusion system as recited in claim 3 wherein said predetermined shape defines a height of at least 2 millimeters and less than 180 millimeters.

6. The spinal fusion system as recited in claim 1 wherein said cover is adapted to be secured to at least one of said adjacent spinal bones.

7. The spinal fusion system as recited in claim 6 wherein said cover is adapted to provide mechanical fixation of said adjacent spinal bones.

8. The spinal fusion system as recited in claim 6 wherein said cover is adapted to be secured to each of said adjacent spinal bones.

9. The spinal fusion system as recited in claim 1 wherein said cover is adapted to be secured to said adjacent spinal bones to fix the spatial relationship between them and substantially simultaneously covering said graft area.

10. The spinal fusion system as recited in claim 1 wherein a single cage is used during a multiple level vertebrectomy or discectomy in place of a plurality of spinal bones or plurality of discs, respectively.

11. The spinal fusion system as recited in claim 1 wherein said cover is fitted to said housing either by mechanical attachment or by floating adjacency allowing for settling and controlled motion of said adjacent spinal bones.

12. The spinal fusion system as recited in claim 1 wherein said housing comprises migration preventers for preventing said housing from migrating toward a spinal cord or other neurological elements after said housing is situated between said adjacent spinal bones.

13. The spinal fusion system as recited in claim 12 wherein said migration preventers comprise at least one tab.

14. The spinal fusion system as recited in claim 12 wherein said migration preventers comprise a plurality of tabs adapted to engage said adjacent spinal bones when said housing is situated therebetween.

15. The spinal fusion system as recited in claim 14 wherein said plurality of tabs are adapted to engage said adjacent spinal bones when said housing is situated therebetween.

16. The spinal fusion system as recited in claim 1 wherein said housing further comprises:
   a first wall portion and a second wall portion, said first and second wall portions being integrally formed into said housing and defining a channel area for receiving said cover.

17. The spinal fusion system as recited in claim 16 wherein said first and second wall portions extend beyond said housing.

18. The spinal fusion system as recited in claim 16 wherein said first and second wall portions each comprising a beveled edge, said cover also comprising beveled edges for mating with said beveled edges of said first and second wall portions when said cover is situated over said opening.

19. The spinal fusion system as recited in claim 18 wherein said first and second wall portions extend beyond said housing and define a plurality of migration preventers for preventing said housing from migrating toward a spinal cord or other neurological structure after said housing is situated between said adjacent spinal bones.

20. The spinal fusion system as recited in claim 19 wherein said migration preventers comprise a plurality of tabs defined by a first wall portion and a second wall portion, said plurality of tabs adapted to a engage said adjacent spinal bones when said housing is situated therebetween.

21. The spinal fusion system as recited in claim 14 wherein said plurality of tabs are adapted to engage said adjacent spinal bones when said housing is situated therebetween.

22. The spinal fusion system as recited in claim 1 wherein said system further comprises at least one migration stop for preventing anterior migration of said housing.

23. The spinal fusion system as recited in claim 22 wherein at least one migration stop cooperates with said cover to prevent said anterior migration.

24. The spinal fusion system as recited in claim 22 wherein said system further comprises a plurality of migration stops.

25. The spinal fusion system as recited in claim 22 wherein said at least one migration stop is a cross members secured to said housing.

26. The spinal fusion system as recited in claim 24 wherein said plurality of migration stops comprises a cross member secured to said housing.

27. The spinal fusion system as recited in claim 19 wherein said system further comprises at least one migration stop for preventing anterior migration of said housing.

28. The spinal fusion system as recited in claim 27 wherein said at least one migration stop cooperates with said cover to prevent said anterior migration.

29. The spinal fusion system as recited in claim 27 wherein said system further comprises a plurality of migration stops.

30. The spinal fusion system as recited in claim 1 wherein said spinal fusion system comprises a plurality of housings each comprising an opening for receiving graft material;
said cover covering said opening of each of said plurality of housings.

31. The spinal fusion system as recited in claim 30 wherein said plurality of housings comprises a first housing adapted to be located between a first pair of spinal bones and a second housing adapted to be located between a second pair of spinal bones, said cover being adapted to be secured to a plurality of spinal bones to thereby cover said openings.

32. The spinal fusion system as recited in claim 30 wherein said cover is situated in operative relationship to said plurality of housings to allow for settling or motion of said adjacent spinal bones.

33. The spinal fusion system as recited in claim 1 wherein said cover comprises at least one resilient detent associated with an opening for permitting a screw to be situated in said opening and adapted to be screwed into said adjacent spinal bones, said at least one resilient detent adapted to prevent said screw from withdrawing from said adjacent spinal bone.

34. The spinal fusion system as recited in claim 33 wherein said at least one resilient detent comprises a spring detent integral with said cover.

35. The spinal fusion system as recited in claim 1 wherein said cover comprises a plate member and an integral lock for preventing withdrawal of at least one screw.

36. The spinal fusion system as recited in claim 35 wherein said plate member comprises a resilient member integrally formed in said member;
said resilient member comprising a detent portion,
said resilient member moving from a home position when said at least one screw is received in said cover and returning to said home position after said at least one screw clears said detent portion.

37. The spinal fusion system as recited in claim 36 wherein said resilient member is generally L-shaped in cross-section.

38. The spinal fusion system as recited in claim 36 wherein said plate member comprises titanium.

39. A spinal bones fusing system comprising:
a housing adapted to be situated between a first spinal bone and a second spinal bone;
said housing being generally U-shaped and cooperating with said first and second spinal bones to define an opening that opens into a graft area for receiving graft material; and
a cover for covering said opening to facilitate preventing anterior migration of said graft material;
said cover being adapted to be secured to at least one of said first or second spinal bones such that it permits said housing to migrate or float relative to said cover while said cover is covering said opening.

40. The spinal bones fusing system as recited in claim 39 wherein said housing comprises a first leg portion, a second leg portion and a joining portion joining said first and second leg portions, said joining portion adapted to be situated between a spinal cord and said opening when said housing is situated between said first and second spinal bones.

41. The spinal bones fusing system as recited in claim 39 wherein said graft area comprises a predetermined shape and defines an anterior graft opening to permit anterior loading of said graft material into said graft area.

42. The spinal bones fusing system as recited in claim 41 wherein said predetermined shape causes said graft material to be formed into a multi-sided fused coupling between said first and second spinal bones.

43. The spinal bones fusing system as recited in claim 41 wherein said predetermined shape defines a height of at least 2 millimeters and less than 180 millimeters.

44. The spinal bones fusing system as recited in claim 39 wherein said cover is adapted to be secured to at least one of said first or second spinal bones.

45. The spinal bones fusing system as recited in claim 44 wherein said cover is adapted to be secured to each of said first and second spinal bones.

46. The spinal bones fusing system as recited in claim 39 wherein said cover is adapted to be secured to said housing.

47. The spinal bones fusing system as recited in claim 39 wherein said housing comprises migration preventers for preventing said housing from migrating toward a spinal cord or other neurological structure after said housing is situated between said spinal bones.

48. The spinal bones fusing system as recited in claim 47 wherein said migration preventers comprise at least one tab.

49. The spinal bones fusing system as recited in claim 47 wherein said migration preventers comprise a plurality of tabs adapted to engage said adjacent spinal bones when said housing is situated therebetween.

50. The spinal bones fusing system as recited in claim 49 wherein said plurality of tabs are adapted to engage said adjacent spinal bones when said housing is situated therebetween.

51. The spinal bones fusing system as recited in claim 39 wherein said housing further comprises:
a first wall portion and a second wall portion, said first and second wall portions being integrally formed into said housing and defining a channel area for receiving said cover.

52. The spinal bones fusing system as recited in claim 51 wherein said first and second wall portions extend beyond said housing.

53. The spinal bones fusing system as recited in claim 51 wherein said first and second wall portions each comprising a beveled edge, said cover also comprising beveled edges for mating with said beveled edges of said first and second wall portions when said cover is situated over said opening.

54. The spinal bones fusing system as recited in claim 51 wherein said first and second wall portions extend beyond said housing and define a plurality of migration preventers for preventing said housing from migrating toward a spinal cord or other neurological structure after said housing is situated between said adjacent spinal bones.

55. The spinal bones fusing system as recited in claim 54 wherein said migration preventers comprise a plurality of tabs defined by said first and second wall portions, said plurality of tabs adapted to engage said first or second spinal bones when said housing is situated therebetween.

56. The spinal bones fusing system as recited in claim 49 wherein said plurality of tabs are adapted to engage said first or second spinal bones when said housing is situated therebetween.

57. The spinal bones fusing system as recited in claim 39 wherein said system further comprises at least one migration stop for preventing anterior migration of said housing.

58. The spinal bones fusing system as recited in claim 39 wherein said spinal bones fusing system further comprises at least one migration stop that cooperates with said cover to prevent said anterior migration of said housing.

59. The spinal bones fusing system as recited in claim 57 wherein said system further comprises a plurality of migration stops.

60. The spinal bones fusing system as recited in claim 59 wherein said plurality of migration stops are cross members secured to said housing.

61. The spinal bones fusing system as recited in claim 57 wherein said at least one migration stop is a cross member secured to said housing.

62. The spinal bones fusing system as recited in claim 44 wherein said system further comprises at least one migration stop for preventing anterior migration of said housing.

63. The spinal bones fusing system as recited in claim 62 wherein said spinal bones fusing system further comprises a cover for covering said opening, said at least one migration stop cooperating with said cover to prevent said anterior migration.

64. The spinal bones fusing system as recited in claim 62 wherein said system further comprises a plurality of migration stops.

65. The spinal bones fusing system as recited in claim 39 wherein said spinal bones fusing system comprises a plurality of housings each comprising an opening for receiving graft material;
said cover covering said opening of each of said plurality of housings.

66. The spinal bones fusing system as recited in claim 65 wherein said plurality of housings comprises a first housing adapted to be located between a first pair of spinal bones and a second housing adapted to be located between a second pair of spinal bones, said cover adapted to be secured to a plurality of spinal bones to thereby cover said openings.

67. The spinal bones fusing system as recited in claim 39 wherein said graft area comprises a length that generally corresponds to a length of a single spinal bone.

68. The spinal bones fusing system as recited in claim 39 wherein said graft area comprises a length that generally corresponds to a length of a plurality of spinal bones.

69. The spinal bones fusing system as recited in claim 39 wherein said cover comprises a plate member and an integral lock for preventing withdrawal of at least one screw.

70. The spinal bones fusing system as recited in claim 69 wherein said plate member comprises a resilient member integrally formed in said plate member;
said resilient member comprising a detent portion,
said resilient member moving from a home position when said at least one screw is received in said cover and returning to said home position after said screw clears said detent portion.

71. The spinal bones fusing system as recited in claim 70 wherein said resilient member is generally L-shaped in cross-section.

72. The spinal bones fusing system as recited in claim 70 wherein said cover comprises a plate comprising titanium.

73. A method for fusing spinal bones together, comprising the steps of:
situating a cage in a graft area between spinal bones, said cage adapted to cooperate with said spinal bones to define an anterior opening for introducing graft material into said graft area;
situating said graft material through said anterior opening and into said graft area; and
covering said anterior opening with a cover;
said cover adapted to be secured to at least one of said spinal bones such that it permits said cage to migrate or float relative to said cover while covering said anterior opening.

74. The method as recited in claim 73 wherein said method further comprises the step of:
inserting said cage between said spinal bones until at least one migration preventer stops said cage from migrating toward a spinal cord or other neurological structure.

75. The method as recited in claim 74 wherein said method further comprises the step of:
inserting said cage between said spinal bones until said at least one migration preventer engages at least one of said spinal bones.

76. The method as recited in claim 73 wherein said covering step further comprises the step of securing a cover to said spinal bones in order to cover said opening.

77. The method as recited in claim 73 wherein said cage comprises a shape generally corresponding to a size of a single spinal bone.

78. The method as recited in claim 73 wherein said cage comprises a shape generally corresponding to a size of multiple spinal bones.

79. The method as recited in claim 73 wherein said method further comprises the step of:
situating a plurality of cages into a plurality of graft areas, each of said plurality of cages cooperating with a plurality of spinal bones to define a plurality of graft openings.

80. The method as recited in claim 79 wherein said method further comprises the step of:
securing a cover to said spinal bones, said cover covering each of said plurality of graft openings.

81. The method as recited in claim 73 wherein said method further comprises the steps of:
  removing said cover; and
  inserting a second cage into a second graft area between two spinal bones, said second cage cooperating with said spinal bones to define a second anterior opening for introducing graft material into said second graft area;
  securing said cover to said spinal bones to cover said anterior opening and said second anterior opening.

82. An implant for facilitating grafting spinal bones together, comprising:
  a housing for situating between said spinal bones, said housing cooperating with said spinal bones to define a graft area and an opening for introducing graft material into said graft opening; and
  a cover adapted to be secured to said spinal bones;
  said cover not being secured to said housing and substantially simultaneously covering said opening after said graft material is situated in said graft area such that it permits said housing to migrate or float relative to said cover mounted over said opening.

83. The implant as recited in claim 82 wherein said opening is an anterior opening.

84. The implant as recited in claim 82 wherein said cover fixes said spinal bones in a predetermined position.

85. The implant as recited in claim 84 wherein said cover permits said housing to move relative to said cover after said cover is adapted to be secured to said spinal bones.

86. The implant as recited in claim 84 wherein said graft area comprises a dimension that generally corresponds to a dimension of a single spinal bone.

87. The implant as recited in claim 84 wherein graft area comprises a dimension that generally corresponds to a dimension of multiple spinal bones.

88. The implant as recited in claim 82 wherein said housing is generally U-shaped.

89. The implant as recited in claim 82 wherein said housing cooperates with said spinal bones to define an anterior opening that permits said graft material to be situated in said graft area after said housing is adapted to be situated between said spinal bones.

90. The implant as recited in claim 82 wherein said housing comprises migration preventers for preventing said housing from migrating toward a spinal cord or other neurological structure after said housing is adapted to be situated between said spinal bones.

91. The implant as recited in claim 90 wherein said migration preventers comprise at least one tab.

92. The implant as recited in claim 90 wherein said migration preventers comprise a plurality of tabs that are adapted to engage said spinal bones when said housing is situated therebetween.

93. The implant as recited in claim 91 wherein said at least one tab is adapted to engage said spinal bones when said housing is situated therebetween.

94. The implant as recited in claim 82 wherein said housing further comprises:
  a first wall portion and a second wall portion, said first and second wall portions being integrally formed into said housing and defining a channel area for receiving said cover.

95. The implant as recited in claim 94 wherein said first and second wall portions define an area for receiving said cover between said first and second wall portions.

96. The implant as recited in claim 94 wherein said first and second wall portions each comprise a beveled edge, said cover also comprising beveled edges for mating with said beveled edges of said first and second wall portions when said cover is situated over said opening.

97. The implant as recited in claim 94 wherein said first and second wall portions comprise elongated portions that extend beyond said housing to define a plurality of migration preventers for preventing said housing from migrating toward a spinal cord or other neurological structure after said housing is situated between said spinal bones.

98. The implant as recited in claim 97 wherein said migration preventers comprise a plurality of tabs defined by said first and second wall portions, said plurality of tabs adapted to engage said spinal bones when said housing is situated therebetween.

99. The implant as recited in claim 98 wherein said plurality of tabs are adapted to engage said spinal bones when said housing is situated therebetween.

100. The implant as recited in claim 82 wherein said implant further comprises at least one migration stop for preventing anterior migration of said housing.

101. The implant as recited in claim 100 wherein said at least one migration stop cooperates with said cover to prevent said anterior migration.

102. The implant as recited in claim 100 wherein said implant further comprises a plurality of migration stops.

103. The implant as recited in claim 102 wherein said plurality of migration stops are cross members secured to said housing.

104. The implant as recited in claim 90 wherein said implant further comprises at least one migration stop for preventing anterior migration of said housing.

105. The implant as recited in claim 104 wherein said at least one migration stop cooperates with said cover to prevent said anterior migration.

106. The implant as recited in claim 105 wherein said implant further comprises a plurality of migration stops.

107. The implant as recited in claim 106 wherein said plurality of migration stops are cross members secured to said housing.

108. The implant as recited in claim 82 wherein said implant comprises a plurality of housings, each defining said opening for receiving graft material;
  said cover covering each opening of each of said plurality of housings after said cover is secured to said spinal bones.

109. The implant as recited in claim 108 wherein said plurality of housings comprises a first housing adapted to be located between a first pair of spinal bones and a second housing adapted to be located between a second pair of spinal bones, said cover adapted to be secured to a plurality of spinal bones to thereby cover said openings while simultaneously fixing said spinal bones relative to each other.

110. The implant as recited in claim 82 wherein said cover comprises a generally planar member and an integral lock for preventing withdrawal of at least one screw after said at least one screw is received in said cover.

111. The implant as recited in claim 110 wherein said generally planar member comprises a resilient member integrally formed in said member;
  said resilient member comprising a detent portion,
  said resilient member moving from a home position in response to said at least one screw being screwed and returning to said home position after said at least one screw clears said detent portion.

112. The implant as recited in claim 111 wherein said resilient member is generally L-shaped in cross-section.

113. The implant as recited in claim 82 wherein said cover comprises a titanium plate.

114. A method for fusing spinal bones together, comprising the steps of:
providing a housing for situating between spinal bones, said housing cooperating with said spinal bones to define an opening for introducing graft material into said graft area after said housing is situated between said spinal bones;
enabling said graft material to be introduced through said opening and into said graft area after said housing is situated between said spinal bones; and
providing a plate adapted to be secured to said spinal bones to fix said spinal bones into a predetermined position relative to each other and to facilitate covering said opening after said graft material is introduced into said graft area such that said housing can float or migrate relative to said plate.

115. The method as recited in claim 114 wherein said method further comprises the step of:
providing a housing comprising at least one migration preventer that enables said housing to be inserted between said spinal bones until at least one migration preventer stops said housing from migrating toward a spinal cord or other neurological structure.

116. The method as recited in claim 115 wherein said method further comprises the step of:
inserting said housing between said spinal bones until said at least one migration preventer engages at least one of said spinal bones.

117. The method as recited in claim 114 wherein said covering step further comprises the step of securing said plate to said spinal bones in order to cover said opening.

118. The method as recited in claim 114 wherein said housing comprises a shape generally corresponding to a size of a single spinal bone.

119. The method as recited in claim 114 wherein said housing comprises a shape generally corresponding to a size of multiple spinal bones.

120. The method as recited in claim 114 wherein said method further comprises the step of:
situating a plurality of housings into a plurality of graft areas, each of said plurality of housings cooperating with a plurality of spinal bones to define a plurality of graft openings.

121. The method as recited in claim 114 wherein said method further comprises the steps of:
providing a plate that can be detachably secured to said spinal bones to permit a second housing to be inserted into a patient, said second housing cooperating with spinal bones to provide a second opening, said plate covering both said opening and said second opening after it is secured to said spinal bones.

122. The method as recited in claim 114 wherein said method further comprises the step of:
providing a housing that is generally U-shaped.

123. A spinal fusion system for use as a prosthetic implant comprising:
a housing dimensioned to be situated between adjacent spinal bones, said housing defining a graft area for receiving a graft or graft-like material for generating a fusion between said adjacent spinal bones;
said housing comprising at least one wall that defines an opening after said housing is situated between said adjacent spinal bones to permit post-placement loading of graft material;
a cover for covering said opening to facilitate preventing anterior migration of said graft material; and
said cover being adapted to be secured to at least one of said adjacent spinal bones such that it permits said housing to migrate or float relative to said cover.

124. The spinal fusion system as recited in claim 123 wherein said housing is generally U-shaped.

125. The spinal fusion system as recited in claim 123 wherein said housing surrounds said graft area and cooperates with said adjacent spinal bones to define a caged area comprising a predetermined shape and defining an anterior opening to permit said post-replacement loading of said graft material.

126. The spinal fusion system as recited in claim 125 wherein said predetermined shape causes said graft material to be formed into a multi-sided fused coupling between said adjacent spinal bones.

127. The spinal fusion system as recited in claim 125 wherein said predetermined shape defines a height of at least 2 millimeters and less than 180 millimeters.

128. The spinal fusion system as recited in claim 123 wherein said cover is adapted to be secured to at least one of said adjacent spinal bones.

129. The spinal fusion system as recited in claim 128 wherein said cover provides mechanical fixation of adjacent spinal bones.

130. The spinal fusion system as recited in claim 129 wherein said cover permits said housing to move in response to motion or settling of said adjacent spinal bones.

131. The spinal fusion system as recited in claim 128 wherein said cover is adapted to be secured to each of said adjacent spinal bones.

132. The spinal fusion system as recited in claim 123 wherein a single cage is used during a multiple level vertebrectomy or discectomy in place of a plurality of spinal bones or plurality of discs, respectively.

133. The spinal fusion system as recited in claim 123 wherein multiple cages are used during a multiple level vertebrectomy or discectomy in place of a plurality of spinal bones or plurality of discs, respectively.

134. The spinal fusion system as recited in claim 123 wherein said cover is fitted to said housing either by mechanical attachment or by floating adjacency allowing for settling and controlled motion of adjacent spinal bones.

135. The spinal fusion system as recited in claim 123 wherein said housing comprises migration preventers for preventing said housing from migrating toward a spinal cord or other neurological elements after said housing is situated between said adjacent spinal bones.

136. The spinal fusion system as recited in claim 135 wherein said migration preventers comprise at least one tab.

137. The spinal fusion system as recited in claim 135 wherein said migration preventers comprise a plurality of tabs that are adapted to engage said adjacent spinal bones when said housing is situated therebetween.

138. The spinal fusion system as recited in claim 137 wherein each of said plurality of tabs are adapted to engage said adjacent spinal bones when said housing is situated therebetween.

139. The spinal fusion system as recited in claim 123 wherein said housing further comprises:
a first wall portion and a second wall portion, said first and second wall portions being integrally formed into said housing and defining a channel area for receiving said cover.

140. The spinal fusion system as recited in claim 139 wherein said first and second wall portions extend beyond said housing.

141. The spinal fusion system as recited in claim 139 wherein said first and second wall portions each comprise a beveled edge, said cover also comprising beveled edges for mating with said beveled edges of said first and second wall portions when said cover is situated over said opening.

142. The spinal fusion system as recited in claim 140 wherein said first and second wall portions extend beyond said housing and define a plurality of migration preventers for preventing said housing from migrating toward a spinal cord or other neurological structure after said housing is situated between said adjacent spinal bones.

143. The spinal fusion system as recited in claim 139 wherein said migration preventers comprise a plurality of tabs defined by said first and second wall portions, said plurality of tabs adapted to engage said adjacent spinal bones when said housing is situated therebetween.

144. The spinal fusion system as recited in claim 123 wherein said system further comprises at least one migration stop for preventing anterior migration of said housing.

145. The spinal fusion system as recited in claim 144 wherein said spinal fusion system further comprises a cover for covering said opening, said at least one migration stop cooperating with said cover to prevent said anterior migration.

146. The spinal fusion system as recited in claim 144 wherein said system further comprises a plurality of migration stops.

147. The spinal fusion system as recited in claim 146 wherein said plurality of migration stops are cross members secured to said housing.

148. The spinal fusion system as recited in claim 145 wherein said at least one migration stop is a cross member secured to said housing.

149. The spinal fusion system as recited in claim 146 wherein said system further comprises a plurality of migration stops preventing anterior migration of said housing.

150. The spinal fusion system as recited in claim 149 wherein said plurality of migration stops cooperate with said cover to prevent said anterior migration.

151. The spinal fusion system as recited in claim 149 wherein said system further comprises two migration stops.

152. The spinal fusion system as recited in claim 123 wherein said spinal fusion system comprises a plurality of housings each comprising an opening for receiving graft material;
said cover covering said opening of each of said plurality of housings.

153. The spinal fusion system as recited in claim 152 wherein said plurality of housings comprises a first housing adapted to be located between a first pair of spinal bones and a second housing adapted to be located between a second pair of spinal bones, said cover adapted to be secured to a plurality of spinal bones to thereby cover said openings.

154. The spinal fusion system as recited in claim 152 wherein said cover is situated in operative relationship to said plurality of housings to allow for settling or motion of said spinal bones.

155. The spinal fusion system as recited in claim 123 wherein said cover comprises at least one resilient detent associated with an opening for permitting a screw to be situated in said opening and adapted to be screwed into a spinal bone, said at least one resilient detent preventing said screw from withdrawing from said spinal bone.

156. The spinal fusion system as recited in claim 155 wherein said at least one resilient detent comprises a spring detent integral with said cover.

157. The spinal fusion system as recited in claim 123 wherein said cover comprises a generally planar member and an integral lock for preventing withdrawal of at least one screw.

158. The spinal fusion system as recited in claim 157 wherein said generally planar member comprises a resilient member integrally formed in said member and defining said integral lock;
said resilient member comprising a detent portion,
said resilient member moving from a home position when said at least one screw is received in said cover and returning to said home position after said at least one screw clears said detent portion.

159. The spinal fusion system as recited in claim 158 wherein said resilient member is generally L-shaped in cross-section.

160. The spinal fusion system as recited in claim 157 wherein said cover defines a generally planar member comprising at least one of the following compositions: titanium, stainless, or carbon fiber.

161. The spinal fusion system as recited in claim 123 wherein said cover comprises an integral lock for locking screws that are adapted to secure said cover to said adjacent spinal bones into a locked position after said screws are adapted to be secured to at least one of said adjacent spinal bones.

162. A method for fusing spinal bones together, comprising the steps of:
removal of diseased or injured spinal bones and/or vertebral disks;
situating either a single cage or a plurality of cages between remaining spinal bones, said cage or cages cooperating with said spinal bones to define an anterior opening for introducing graft or graft-like material with the purpose of generating a fusion between adjacent spinal bones into said graft area;
situating graft material through said anterior opening and into said graft area;
covering said anterior opening with a cover such that said cover permits either said single cage or said plurality of cages to migrate or float relative to said cover while performing said covering step; and
securing said cover to a plurality of spinal bones.

163. The method as recited in claim 162 wherein said method further comprises the step of:
inserting said single cage or plurality of cages between said spinal bones until at least one migration preventer stops said cage from migrating toward a spinal cord or other neurological structure.

164. The method as recited in claim 163 wherein said method further comprises the step of:
inserting said single cage or plurality of cages between said spinal bones until said at least one migration preventer engages at least one of said spinal bones.

165. The method as recited in claim 162 wherein said covering step further comprises the step of securing a cover to said spinal bones in order to cover said opening.

166. The method as recited in claim 162 wherein at least one of said single cage or plurality of cages comprises a shape generally corresponding to a size of a single spinal bone.

167. The method as recited in claim 162 wherein at least one of said single cage or plurality of cages comprises a shape generally corresponding to a size of multiple spinal bones.

168. The method as recited in claim 162 wherein at least one of said single cage or plurality of cages comprises a shape generally corresponding to a size of a single vertebral disk.

169. The method as recited in claim 162 wherein at least one of said single cage or plurality of cages comprises a shape generally corresponding to a size of multiple vertebral disks.

170. The method as recited in claim 162 wherein said method further comprises the step of:

situating a plurality of cages into a plurality of graft areas, each of said plurality of cages cooperating with a plurality of spinal bones to define a plurality of graft openings.

171. The method as recited in claim 170 wherein said method further comprises the step of:

securing a cover to said spinal bones, said cover covering each of said plurality of graft openings.

172. The method as recited in claim 162 wherein said method further comprises the steps of:

removing said cover;

inserting a second cage into a second graft area between two spinal bones, said second cage cooperating with said spinal bones to define a second anterior opening for introducing graft material into said second graft area; and securing a second cover to said spinal bones to cover said anterior opening and said second anterior opening, said second cover being longer than said cover.

* * * * *

UNITED STATES PATENT AND TRADEMARK OFFICE
CERTIFICATE OF CORRECTION

| | |
|---|---|
| PATENT NO. | : 7,182,782 B2 |
| APPLICATION NO. | : 10/675361 |
| DATED | : February 27, 2007 |
| INVENTOR(S) | : David Louis Kirschman |

It is certified that error appears in the above-identified patent and that said Letters Patent is hereby corrected as shown below:

Column 2, Line 64, please delete "FIG." and insert --FIGS.-- therefor.

Column 3, Line 36, please delete "FIG." and insert --FIGS.-- therefor.

Column 3, Line 38, please delete "a" and insert --an-- therefor.

Column 3, Line 65, please delete "FIG." and insert --FIGS.-- therefor.

Column 3, Line 66, please delete "cross bars" and insert --crossbars-- therefor.

Column 4, Line 12, please insert --.-- after the word together.

Column 4, Line 65, please delete "30" and insert --38-- therefor.

Column 5, Line 1, please delete "32" and insert --38-- therefor.

Column 5, Line 40, please delete "edges" and insert --sides-- therefor.

Column 6, Line 32, please delete ")" after B.

Column 6, Line 42, please delete "cross bars" and insert --crossbars-- therefor.

Column 6, Line 46, please delete "cross bars" and insert --crossbars-- therefor.

Column 6, Line 50, please delete "cross bars" and insert --crossbars-- therefor.

Column 6, Line 51, please delete "cross bars" and insert --crossbars-- therefor.

Column 7, Line 63, please delete "48" and insert --38-- therefor.

Column 9, Line 18, please delete "90" and insert --94 (Fig. 29)-- therefor.

Column 9, Line 32, please delete "cross bars" and insert --crossbars-- therefor.

Signed and Sealed this
Fifth Day of June, 2012

David J. Kappos
*Director of the United States Patent and Trademark Office*

CERTIFICATE OF CORRECTION (continued)
U.S. Pat. No. 7,182,782 B2

Column 9, Line 35, please delete "32" and insert --38-- therefor.

Column 10, Line 2, Claim 3, please delete "," after the word surrounds.

Column 11, Line 8, Claim 20, please delete "a" after the word to.

Column 11, Line 24, Claim 25, please delete "is a" and insert --are-- therefor.

Column 14, Line 18, Claim 70, please delete "said screw" and insert --said at least one screw-- therefor.

Column 14, Line 51, Claim 76, after the second word "said" please insert --anterior--.

Column 20, Line 63, Claim 165, after the second word "said" please insert --anterior--.